(12) United States Patent
Mikhail et al.

(10) Patent No.: US 10,737,057 B1
(45) Date of Patent: Aug. 11, 2020

(54) MULTIPORT SYRINGE SYSTEM FOR USE WITH A URINARY CATHETER

(71) Applicant: Albert A. Mikhail, Sherman Oaks, CA (US)

(72) Inventors: Albert A. Mikhail, Sherman Oaks, CA (US); Corollos Samir Abdelshehid, Bakersfield, CA (US)

(*) Notice: Subject to any disclaimer, the term of this patent is extended or adjusted under 35 U.S.C. 154(b) by 148 days.

(21) Appl. No.: 15/822,103

(22) Filed: Nov. 24, 2017

Related U.S. Application Data

(60) Provisional application No. 62/426,583, filed on Nov. 27, 2016.

(51) Int. Cl.
| | | |
|---|---|---|
| A61M 39/00 | (2006.01) | |
| A61M 39/10 | (2006.01) | |
| A61M 39/22 | (2006.01) | |
| A61M 25/00 | (2006.01) | |
| A61M 5/315 | (2006.01) | |
| A61M 3/02 | (2006.01) | |
| A61M 25/10 | (2013.01) | |
| A61M 1/00 | (2006.01) | |
| A61M 5/31 | (2006.01) | |

(52) U.S. Cl.
CPC ...... *A61M 25/0017* (2013.01); *A61M 1/0021* (2013.01); *A61M 3/0283* (2013.01); *A61M 5/31513* (2013.01); *A61M 25/10185* (2013.11); *A61M 39/10* (2013.01); *A61M 2005/3125* (2013.01); *A61M 2005/3128* (2013.01); *A61M 2205/0216* (2013.01); *A61M 2210/1085* (2013.01)

(58) Field of Classification Search
CPC ............ A61M 25/0075; A61M 39/223; A61M 2039/229; A61M 25/0017; A61M 25/10185; A61M 25/1025; A61M 1/0021; A61M 1/0023; A61M 3/0283; A61M 5/31513; A61M 39/00; A61M 39/10; A61M 2039/1033; A61M 2039/3128; A61M 2039/3125; A61M 2210/1085; A61M 2210/1089

See application file for complete search history.

(56) References Cited

U.S. PATENT DOCUMENTS

| | | | |
|---|---|---|---|
| 2,854,027 A | | 9/1958 | Kaiser et al. |
| 3,344,785 A | * | 10/1967 | Hamilton ............ A61M 1/0062 604/6.1 |
| 3,780,736 A | | 12/1973 | Chen |
| 4,784,637 A | * | 11/1988 | Ryder ................ A61M 1/0062 604/236 |
| 4,895,562 A | | 1/1990 | Lopez |

(Continued)

*Primary Examiner* — Quynh-Nhu H. Vu

(57) ABSTRACT

A medical syringe with at least three ports, in conjunction with a urinary catheter, can be used for closed manual irrigation of a bladder. The three syringe ports are located on a port body. Each of the three syringe ports can be manually selected by rotating a barrel that has a closed end located inside the cup-shaped port body. Rotation of the barrel inside the port body occurs about an axis that is aligned with the central axis of the hollow cylindrical barrel. The system is configured to selectively fill the syringe with an input fluid, irrigate the bladder by passing fluid into and out of the urinary catheter, and drain bladder contents into a drainage vessel without ever needing to remove the syringe from the catheter.

20 Claims, 21 Drawing Sheets

(56) References Cited

U.S. PATENT DOCUMENTS

| | | | |
|---|---|---|---|
| 4,904,245 A * | 2/1990 | Chen | A61M 3/0233 |
| | | | 137/625.47 |
| 5,074,334 A | 12/1991 | Onodera | |
| 5,443,447 A * | 8/1995 | Kassis | A61M 29/00 |
| | | | 604/24 |
| 5,466,228 A * | 11/1995 | Evans | A61M 39/223 |
| | | | 137/625.47 |
| 6,457,488 B2 * | 10/2002 | Loo | A61M 39/223 |
| | | | 137/625.47 |
| 6,953,450 B2 * | 10/2005 | Baldwin | A61M 39/223 |
| | | | 137/625.23 |
| 6,976,974 B2 | 12/2005 | Houde et al. | |
| 7,997,304 B2 | 8/2011 | Ranalletta et al. | |
| 9,320,846 B2 * | 4/2016 | Burns | A61M 5/482 |
| 2002/0151854 A1 * | 10/2002 | Duchon | A61B 6/504 |
| | | | 604/197 |
| 2003/0195478 A1 | 10/2003 | Russo | |
| 2007/0156104 A1 * | 7/2007 | Lockwood | A61M 1/0031 |
| | | | 604/305 |
| 2009/0099552 A1 * | 4/2009 | Levy | A61M 39/10 |
| | | | 604/533 |
| 2009/0182309 A1 * | 7/2009 | Muffly | A61M 39/1011 |
| | | | 604/535 |
| 2009/0221989 A1 | 9/2009 | Najafi et al. | |
| 2010/0185040 A1 * | 7/2010 | Uber, III | A61M 5/007 |
| | | | 600/5 |
| 2010/0268118 A1 * | 10/2010 | Schweiger | A61M 39/223 |
| | | | 600/573 |
| 2018/0117297 A1 * | 5/2018 | Allard | A61M 39/105 |

* cited by examiner

MULTIPORT SYRINGE SYSTEM FOR USE WITH A URINARY CATHETER

This application claims benefit of U.S. Provisional Patent Application Ser. No. 62/426,583 filed 27 Nov. 2016, the entire disclosure of which is incorporated by reference herein.

BACKGROUND

The present invention relates to systems and methods for irrigation and/or drainage of an open or closed body cavity in human or veterinary medicine using a syringe having at least three selectable ports to allow at least three phases of an irrigation process to be performed in a closed system. Such multiphase syringe systems and methods could be used in conjunction with an indwelling urinary catheter that is passed through the urethra or the abdomen into the bladder. It could be used for gastrointestinal purposes for nasogastric tube irrigation, medical feeding and rectal tube applications. It could also be used in other medical applications that require irrigations, infusions, instillation, or drainage of various materials or medications.

In the medical field, irrigation of various body cavities is used to introduce medical therapy or remove/drain various matter such as blood products, mucous, gastrointestinal material, abscess fluid, ear wax, and genitourinary material. Urinary tract surgeries, such as prostate surgery or transurethral resection, typically require the insertion of an indwelling urinary catheter to irrigate and drain the bladder. One example of a device that can be used in such surgical procedures is a urinary catheter. A suprapubic catheter that is inserted through the abdomen into the bladder is another example. Cavities other than the bladder can be irrigated, drained, and/or instilled with other medical therapies in a similar fashion. One example would be nasogastric intubation into the stomach.

Catheters can have multiple lumens (i.e. channels) connecting a body cavity with the outside world. For example, when using a two-lumen urinary catheter for irrigation, one lumen is used for inflating an internal retention balloon and a second lumen can be used for irrigation and drainage. In this configuration, one end of this second lumen would be located in the body cavity and the other end would typically be detachably connected to a manually operated piston syringe for filling, instilling, irrigation, and drainage—a process known as manual (or hand) irrigation. The manual irrigation process typically involves the following steps:
(a) filling the syringe with an irrigating (clean or sterile) solution by placing the tip of the syringe into a container of the solution while manually retracting the piston;
(b) placing the tip of the syringe onto the end of the second lumen of the catheter;
(c) filling the bladder with the irrigating solution by emptying the contents of the syringe into the cavity;
(d) using the syringe to withdraw the material to be flushed (irrigating solution plus blood clots, debris, purulent material, and/or accumulated body tissue) from the bladder;
(e) removing the syringe from the second lumen of the catheter;
(f) emptying the bladder contents from the syringe into a waste container; and
(g) repeating the process as often as necessary, which means the system is opened repeatedly, exposing the catheter lumen and the clean or sterile input fluid to environmental contaminants.

A three-lumen urinary catheter has three channels that can connect to the body cavity. In one configuration, the first lumen is used for the internal retention balloon and the second lumen can be used for performing the same manual irrigation steps that were described for the two-lumen catheter. The third lumen in this configuration can be used for continuous gravity filling of the cavity with an irrigating solution. In another configuration of a three-lumen urinary catheter, the first lumen is for the internal retention balloon, the second is for continuous gravity filling of the cavity with an irrigating solution, and the third is for continuous gravity drainage of the cavity, a configuration called continuous bladder irrigation. The three-lumen urinary catheter system could be converted from the first configuration (manual irrigation) to the second configuration (continuous irrigation) by removing the syringe and replacing it with a line for providing continuous gravity drainage.

The most common systems and methods currently being used for irrigating a bladder require that the system must be opened, or broken repeatedly while irrigating, or when medicine or materials need to be instilled or infused, or when a three-lumen urinary catheter must be changed from manual irrigation to continuous irrigation. Opening an irrigation circuit creates a risk of infection or contamination of the body cavity being irrigated. It can contaminate the clean input fluid source. It can also cause spillage of the input fluid source or drained material, which poses a risk of infecting or contaminating the patient, the operator performing the irrigation, and/or the surrounding equipment and facility. It is desired to have a simple, cost effective, and easy to use closed system that reduces the risk of spillage and contamination. Such a system should also maintain sterility, especially when intermittent irrigation is needed or when manual irrigation is needed during continuous irrigation. Ideally, the system would reduce the risk of catheter or drain associated infections, reduce staffing time needed to clean the spillage from manual irrigation. The system should also reduce the risk of contamination of the cavity, the tubing system, the input fluid source, the patient, any staff member, other patients, and any surrounding equipment and the facility where the system is located. A well-designed system could be left in place for an entire duration/hospitalization for intermittent manual irrigation, whether continuous irrigation is needed or not. Such a system could be used for on-demand manual irrigation with either a two-lumen or a three-lumen urinary catheter. The system could have a manually operable plunger that could have a limiter and a locking mechanism that sets the plunger into a partially open position in the barrel. This locking mechanism could prevent inadvertent insertion or retraction of the plunger in the barrel. The partially open position allows for continuous drainage through the barrel. A simple, cost-effective, and easy-to-use system that doesn't need to be opened, could also be fastened to the patient or in the vicinity of the cavity to prevent tension or dislodging of the syringe from the circuit. The system could be latex free. The system could have universal application. The system could include other features such as the use of bacteriostatic or antibacterial coating on part or all of the system. The system could include a splashguard to minimize spillage if the system is accidentally opened. The system could include a catheter tip fastener that locks the catheter lumen to a catheter port or line on an irrigating device to prevent accidental dislodging of the catheter tip and urinary catheter connection.

BRIEF DESCRIPTION OF THE DRAWINGS

The present disclosure is described in conjunction with the appended figures in which.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, those skilled in the art will know that different materials, manufacturing processes, fastening systems, configurational arrangements, and components may be substituted.

1. Definitions

For purposes of describing embodiments of the present invention and claims, a syringe is defined as a vessel with a nozzle and a piston, bulb, bellows, or other volume-changing element for drawing in and ejecting a fluid for the purpose of cleaning or clearing a body cavity, or for introducing material into the body cavity.

For purposes of describing embodiments of the present invention and claims, a catheter is defined as a tube made of medical grade materials configured for insertion into a body cavity, duct, or vessel to provide drainage, administration of fluids or gases, irrigation and/or access by surgical instruments.

For purposes of describing embodiments of the present invention and claims, a lumen is a fluid channel within a hollow tubular structure (such as a catheter).

2. Typical Prior Art Irrigation Systems and Methods

Figure 1A:
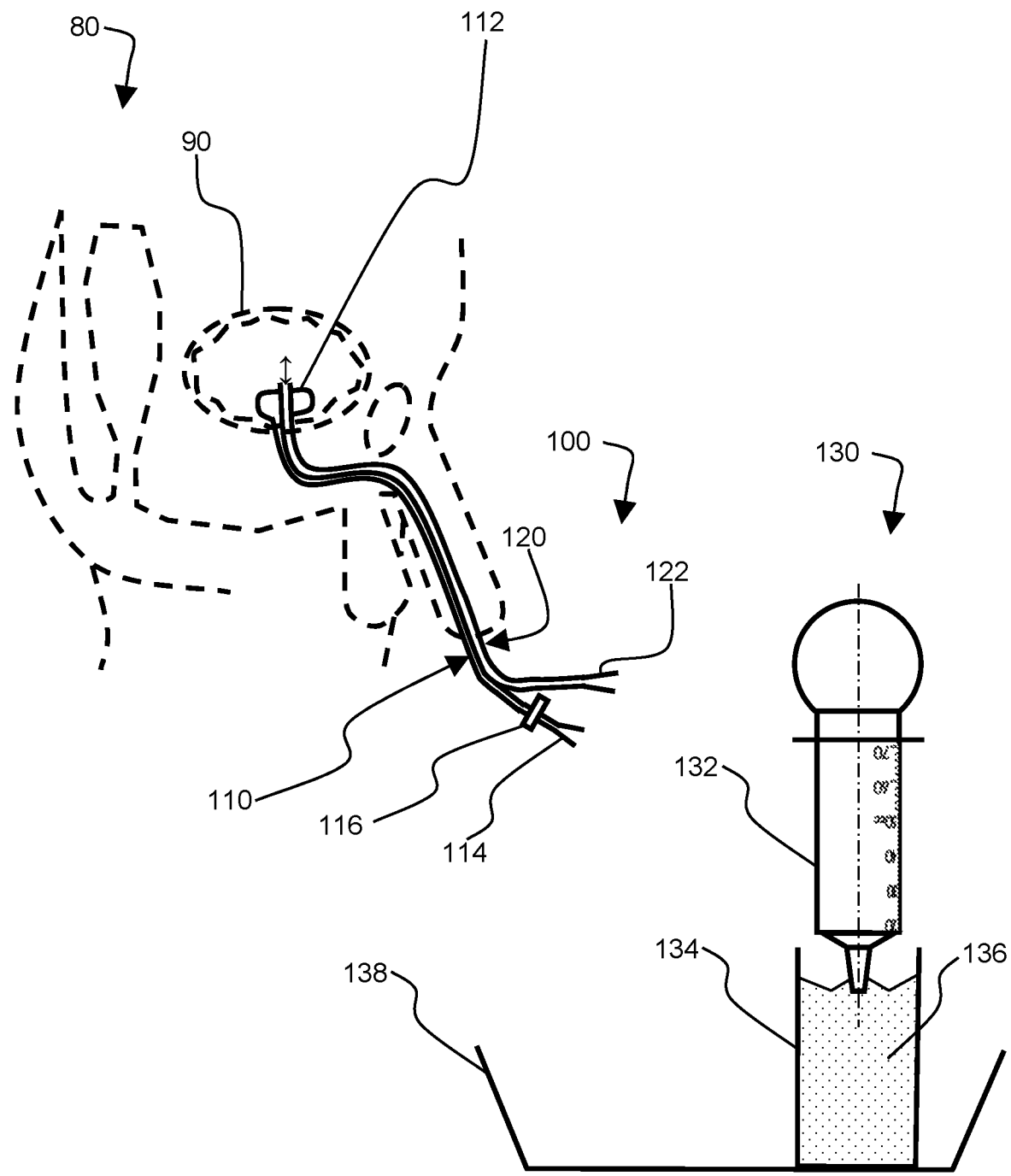
FIG. 1A shows a prior art manual irrigation and drainage system comprising a two-lumen urinary catheter, a single port bulb syringe, an irrigating solution reservoir, and a tray for collecting material that has been flushed out of a bladder.
Figure 1B:
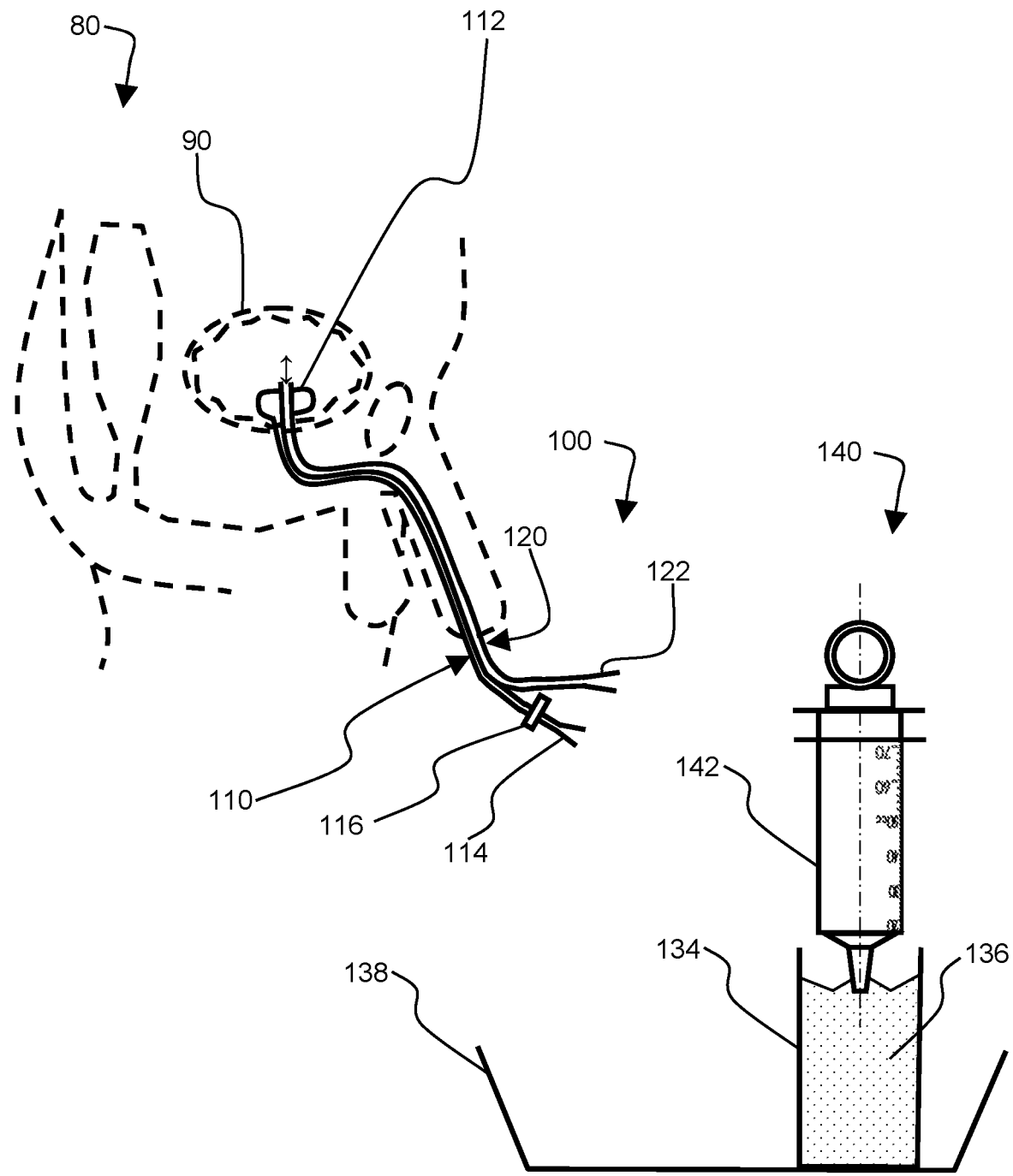
FIG. 1B shows a prior art system similar to FIG. 1A with a single port plunger syringe instead of a bulb syringe.

FIG. 1A and FIG. 1B shows two variations on a typical system used for manual irrigation and drainage of a bladder. These prior art systems are simple and inexpensive, but they are open systems that can easily result in spills, mixing/contaminating of the clean/sterile input fluid with bladder drainage material, and the exposure of a urinary catheter lumen 120 to the outside environment. Referring to the prior art systems shown in FIG. 1A and FIG. 1B, a patient is shown in dotted lines at 80. The patient has a bladder shown at 90. In this case, the patient is a male. Embodiments of the systems and methods shown here and in other figures could also be used on female patients or in animals and they could be used for other body cavities, in configurations capable of being understood by anyone skilled in the art.

FIG. 1A and FIG. 1B show a two-lumen urinary catheter 100. FIG. 1A shows a manual irrigation kit that uses a bulb syringe 130. FIG. 1B shows a manual irrigation kit that uses a plunger-type syringe. The two-lumen catheter 100 comprises a balloon inflation lumen 110 and an irrigation lumen 120. The balloon inflation lumen 110 comprises a urinary catheter balloon 112, a balloon inflation port 114, and a balloon inflation clamp 116. The irrigation lumen 120 comprises an irrigation port 122. The two-lumen urinary catheter 100 is inserted into the bladder 90 of the patient 80 and held in place by inflating a urinary catheter balloon 112 through the balloon inflation lumen 110, by inserting a fluid through the balloon inflation port 114, and then holding the fluid in the balloon 112 by the balloon inflation valve 116. The urinary catheter balloon 112 helps to hold the two-lumen urinary catheter 100 in place in the bladder 90. The second lumen of the two-lumen urinary catheter 100 is an irrigation lumen 120 that serves as a hand (or manual) irrigation and drainage channel between the bladder 90 and anything in the outside world that may be attached to it.

Further referring to FIG. 1A and FIG. 1B, the manual irrigation kit 130 or 140 comprises a bulb syringe 132 or a plunger syringe 142, an input fluid reservoir 134 containing a clean or sterile input fluid 136, and a drainage tray 138. The syringe could be any manually operated vessel for drawing in and pumping out fluid such as the bulb syringe that is shown at 132 in FIG. 1A, a plunger-type syringe, shown at 142 in FIG. 1B, a syringe that uses bellows, or any other vessel for pumping a fluid capable of being understood by anyone skilled in the art. It should be noted that the syringes 132 and 142 used in the prior art shown in FIG. 1A and FIG. 1B have only one port for receiving and ejecting a fluid. The two-lumen catheter 100 and the manual irrigation kits (130 or 142) are typically each purchased as sterile disposable items. The catheter 100 can be used in a patient for an extended period of time. Many irrigation kits (130 and 140) might be used as input fluid is consumed and as effluent from the bladder needs to be disposed. The input fluid reservoir 134 and the waste container 138 are open vessels that can easily be contaminated or spilled. The syringe (132 or 142) must be attached and detached from the irrigation port 122 to manually irrigate and drain the bladder. This means that the irrigation system must be opened and closed frequently. It means that the bladder 90 can easily be exposed to the external environment. It also means that bladder contents can potentially contaminate the operator, patient, and surrounding equipment and facility.

Figure 2:
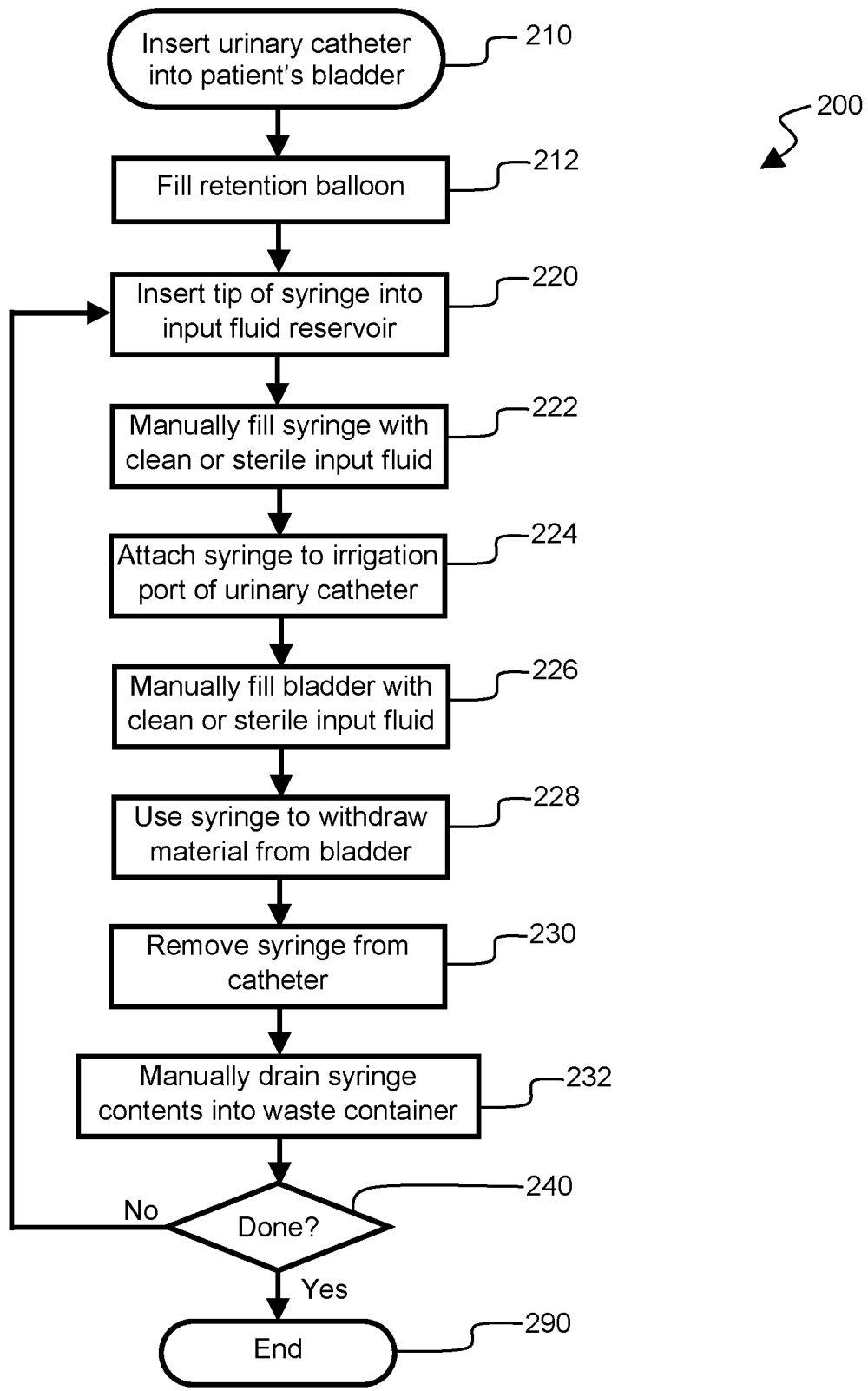
FIG. 2 provides a flowchart of a method for using the system illustrated in FIG. 1A or FIG. 1B.

The prior art systems shown in FIG. 1A and FIG. 1B, can be operated by using the prior art open system manual irrigation method shown at 200 in FIG. 2. This process begins by inserting a urinary catheter into the patient, a step shown at 210. Then the retention balloon is filled 212, which retains one end of the catheter in the bladder. The tip of the syringe (132 in FIG. 1A or 142 in FIG. 1B) is then inserted into an input fluid reservoir, a step shown at 220. The syringe (132 in FIG. 1A or 142 in FIG. 1B) is then manually filled with clean or sterile input fluid, a step shown at 222. This process of filling the syringe depends upon the type of syringe being used. The syringe is then attached to the irrigation port of the urinary catheter 224 and the bladder is then manually filled with the clean or sterile fluid that is in the syringe 226. At that point, the syringe could be removed from the irrigation port of the urinary catheter (a step not shown in FIG. 2) and more irrigation solution added to the bladder by repeating steps 220, 222, 224, and 226, or the syringe could be used to withdraw material from the bladder, as shown in step 228. The material removed from the bladder in step 228 can be a combination of irrigating solution and material to be removed from the bladder, such as blood clots, debris, accumulated body tissue, etc. This material fills the syringe. The syringe (132 in FIG. 1A or 142 in FIG. 1B) is then removed from the catheter, as shown at 230, and the contents of the syringe are then drained into the waste container, typically by reducing the volume of the syringe. The sequence from step 220 to step 232 is repeated as many times as necessary until the hand irrigation is done, as shown by the decision box 240. Once hand irrigation is done, the hand irrigation process ends, as shown in step 290.

Figure 3:
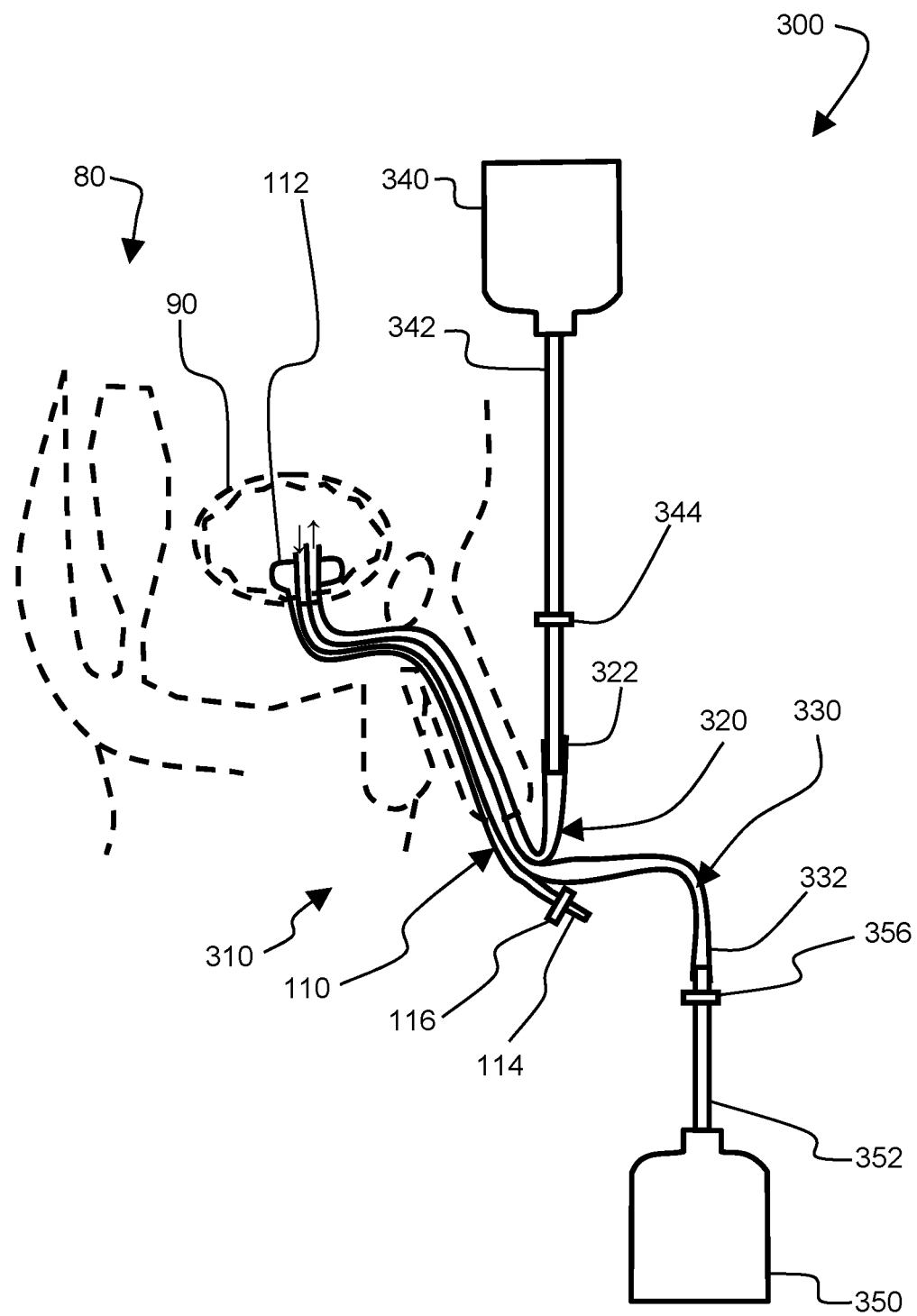
FIG. 3 shows a prior art system for continuous bladder irrigation (i.e. continuous gravity filling and drainage)

Once the hand irrigation process ends, continuous gravity irrigation can be used to continue the irrigation process. In the prior art, this required using a three-lumen urinary catheter and reconfiguring the connections to that shown in FIG. 3. Referring to FIG. 3, the same patient and bladder are shown at 80 and 90, respectively. A continuous gravity irrigation system is shown at 300. This system 300 uses a three-lumen urinary catheter, shown at 310. The three-lumen catheter 310 comprises a balloon inflation lumen 110, an input fluid lumen 320 and a drainage lumen 330. The balloon inflation lumen comprises the same urinary catheter balloon 112, balloon inflation port 114, and balloon inflation valve 116 that were illustrated in FIG. 1A and FIG. 1B. The input fluid lumen 320 comprises an input fluid port 322. The drainage lumen 330 comprises a drainage lumen port 332.

Further referring to FIG. 3, an input fluid source 340 is attached to the input fluid port 322 using an input line (or tube) 342 and there is a usually an input line clamp 344 on the input line 342 that can be used when the input fluid source 340 must be replaced because it is empty or when the supply of input fluid needs to be turned off or regulated. Similarly, there is a drainage vessel 350 attached to the drainage lumen port 332 using a drainage line (or tube) 352 and there is usually a drainage line clamp valve 356 on the drainage line 352 that can be used when the drainage vessel 350 must be replaced because it is full, or when drainage flow needs to be turned off or regulated.

3. Multiphase Syringe Configurations

Figure 4:
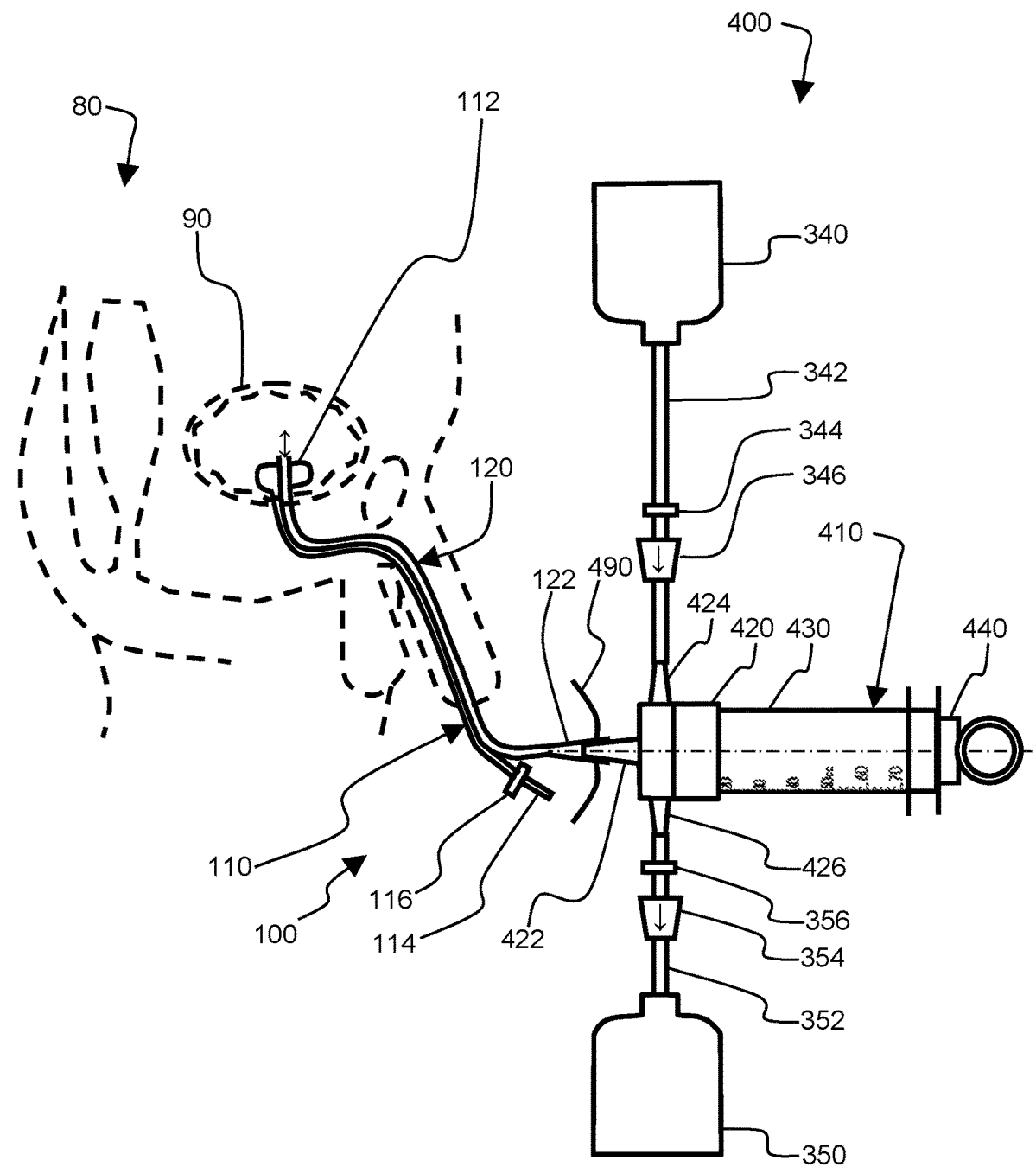
FIG. 4 shows a manual irrigation and drainage system comprising a 3-port 3-position syringe and a two-lumen urinary catheter that has three operational phases.
Figure 5:
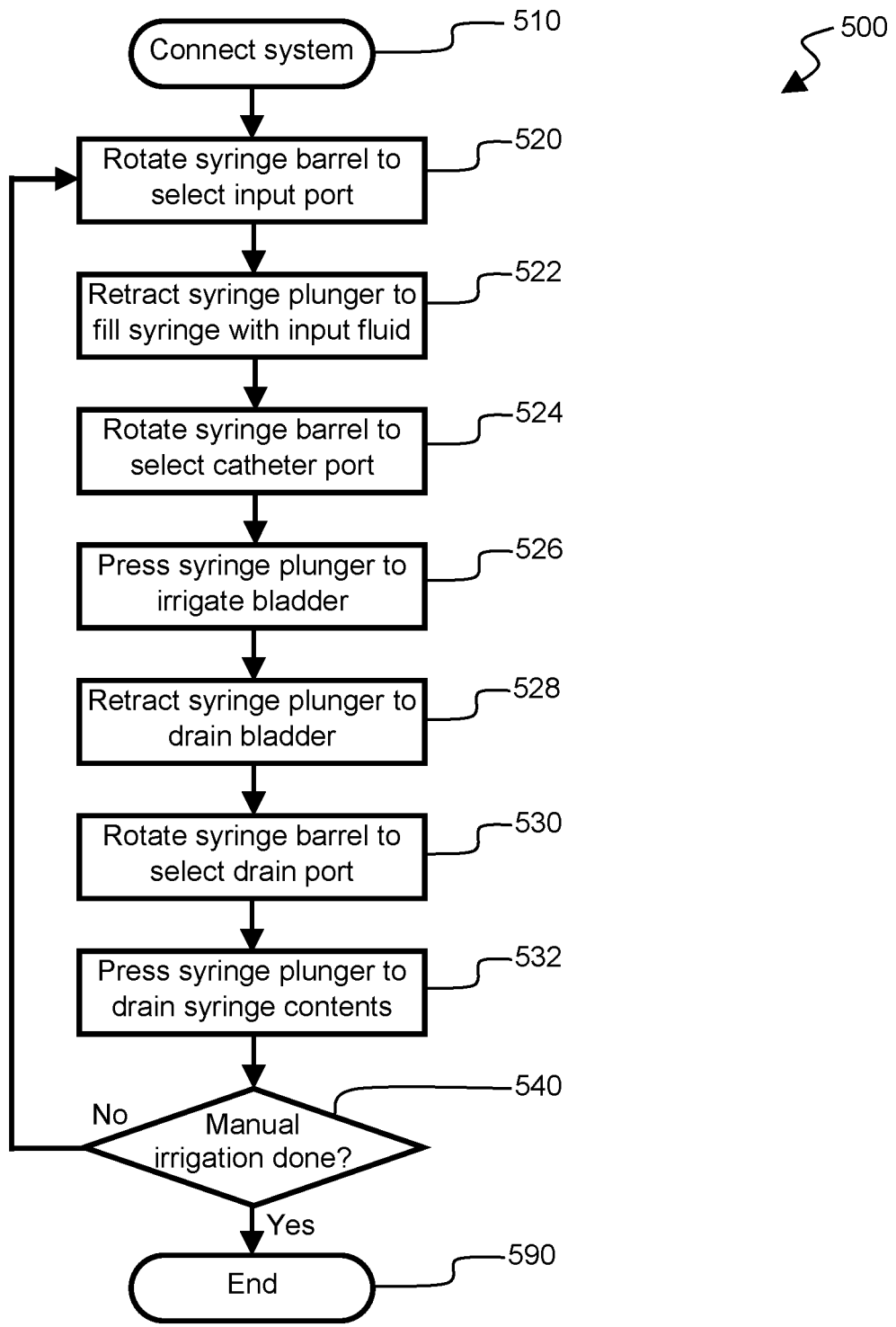
FIG. 5 provides a flowchart of a method for using the system illustrated in FIG. 4.

FIG. 4 shows an embodiment of the present invention that can accomplish all of the functions that were shown and described in FIG. 1A, FIG. 1B and FIG. 2 and is also a closed system. FIG. 5 illustrates a sequence of steps for using the system shown in FIG. 4 to perform manual hand irrigation. Referring to FIG. 4, a patient is shown at 80 and a closed manual irrigation system is shown at 400. Just like in the systems shown in FIG. 1A, FIG. 1B and FIG. 3, the patient is a male, but embodiments could also be used on female patients or in animals, in a configuration capable of being understood by anyone skilled in the art. The closed manual irrigation system 400 comprises the same two-lumen urinary catheter and its various components (110, 112, 114, 116, 120, and 122) that were shown in FIG. 1A and FIG. 1B. Also shown are the same input fluid source 340, input fluid line 342, input line clamp valve 344, drainage vessel 350, drainage line 352, and drainage line clamp valve that were shown in FIG. 3. The system shown in FIG. 4 also includes an optional check valve 346 on the input line. This input line optional check valve can prevent fluids and material from the bladder 90 from contaminating the input fluid in the input fluid source 340 by preventing flow in the input fluid line 342 toward the input fluid source 340 (i.e. preventing reverse flow).

The new component in FIG. 4 is the three-port three-position syringe shown at 410 and the way it is connected to the other components. The three-port three-position syringe 410 comprises a syringe port body, shown at 420, a syringe barrel, shown at 430, and a syringe plunger, shown at 440. The syringe port body 420 comprises three ports: a catheter port 422 that connects to the irrigation port 122; an input port 424 that connects to the input fluid line 342; and a drainage port 426 that connects to the drainage line 352. The syringe barrel 430 can rotate inside port body 420 to select which of the three ports (422, 424, or 426) to connect to the hollow interior of the syringe barrel 430 as will be described and illustrated in more detail later. The syringe plunger 440 can slide in and out of the barrel 430 to pump fluid in or out through the selected port (422, 424, or 426) as will be described and illustrated in more detail later.

Further referring to FIG. 4, the flow in the input fluid line 342 should only be in one direction, away from the input fluid source 340. This can be controlled by an optional input fluid check valve 346 placed in the input fluid line. The flow of fluid from the input fluid source 340 through the input fluid line 342 should occur when the syringe barrel 430 has been rotated inside the port body 420 to provide a fluid path between the input port 424 and the interior of the barrel 430, the input line clamp valve 344 is open and the plunger 440 is being retracted from barrel 430, as will be described and illustrated in more detail later.

The flow in the irrigation lumen 120 can be in two directions. This flow will occur when the syringe barrel 430 has been rotated inside the port body 430 to provide a fluid path between the catheter port 422 and the interior of the barrel 430. Fluid will irrigate the bladder 90 when the plunger 440 is pressed into the barrel 430. Fluid and/or material can be drained from the bladder 90 when the plunger 440 is retracted from the barrel 430.

The flow in the drainage line 352 should only be in one direction, away from the multiport syringe 410. This can be controlled by an optional drainage check valve, shown at 354. The optional drainage check valve 354 prevents the flow of fluid in the drainage line 352 from the waste vessel 350 to the syringe 410 (i.e. reverse flow in the drainage line 352). The flow of fluid in the drainage line 352 should occur when the syringe barrel 430 has been rotated inside the port body 420 to provide a fluid path between the drainage port 426 and the interior of the barrel 430 as the plunger 440 is being pressed into the barrel 430, as will be described and illustrated in more detail later.

FIG. 4 also shows an optional splash shield (splashguard) at 490. The splash shield 490 can be mounted over the catheter port 422 and/or the irrigation port 122. The splash shield 490 can reduce the possibility that user and patient would be splashed with bodily fluids if the catheter port 422 becomes disconnected from the irrigation port 122. The splash shield 490 could be attached to a part of the urinary catheter 100 or the splash shield could be attached to a part of the syringe 490. The splash shield 490 could be permanently attached or the splash shield 490 could be user detachable.

The system shown in FIG. 4 can be operated by using the manual irrigation process shown in FIG. 5. This process begins by connecting the system to the patient, shown in step 510. The syringe barrel is then rotated to select the input (or fill) port, as shown at step 520. Once the input (or fill) port has been selected 520, the syringe plunger is retracted to fill the syringe with input fluid, as shown at step 522. Then the syringe barrel is rotated to select the catheter port, a step shown at 524. With the catheter port selected 524, the syringe plunger is pressed into the syringe body to irrigate the bladder in the step shown at 526. This is followed by a retraction of the syringe plunger to drain the bladder, as shown at the step labeled 528. Next, the syringe barrel is rotated to select the drain (or drainage) port, a step shown at 530. With the drain (or drainage) port selected 530, the syringe plunger is pressed into the syringe barrel to drain the syringe contents, as shown at 532. The sequence from step 520 to step 532 is repeated as many times as necessary until the hand irrigation is done, as shown by the decision box 540. Once hand irrigation is done, the hand irrigation process ends, as shown in step 590. Once the hand irrigation process ends, continuous gravity drainage could continue if the catheter lumen 122 is directly connected to the drainage line 352.

Figure 6:
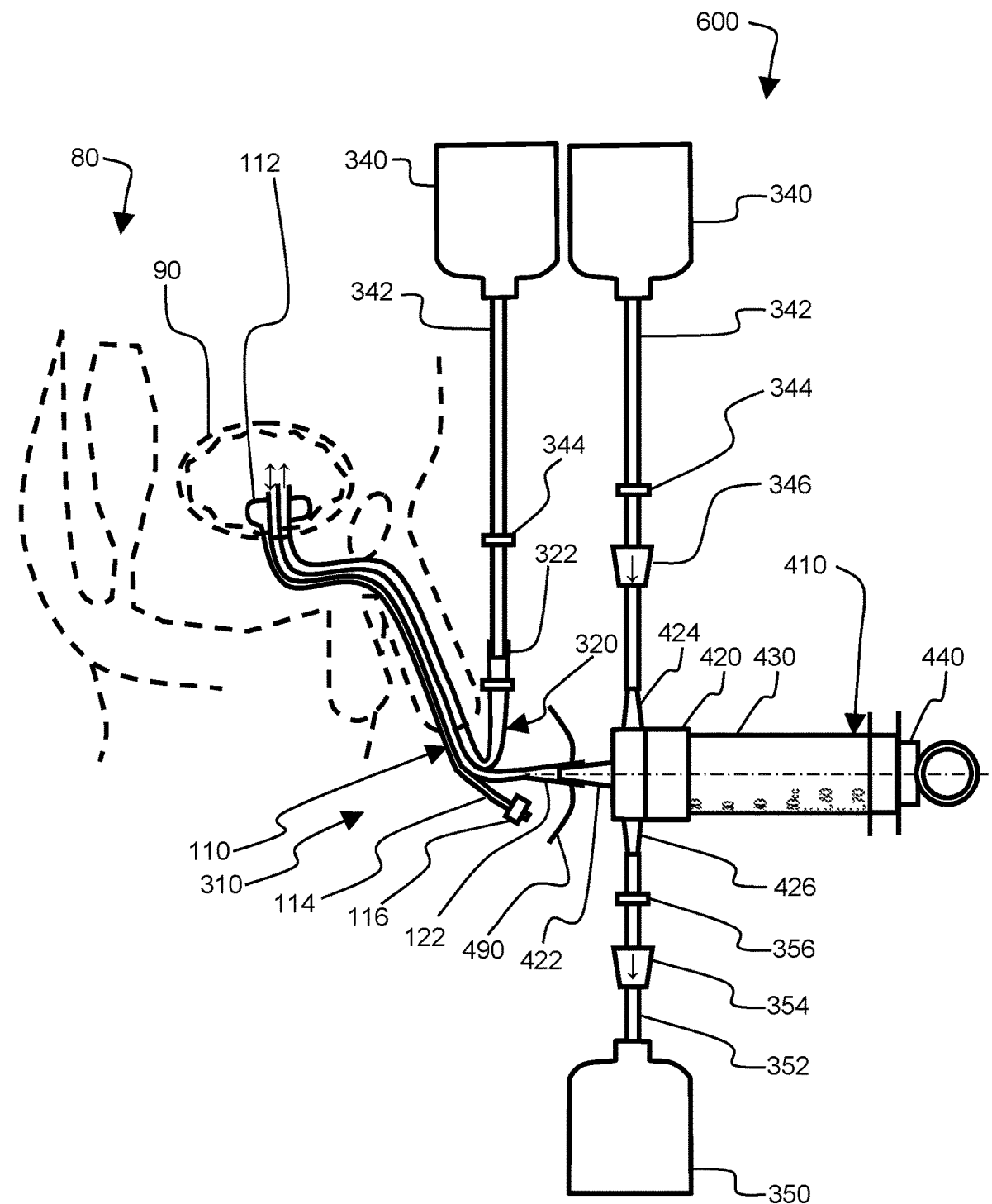
FIG. 6 shows the syringe of FIG. 4 in a system comprising a 3-lumen urinary catheter in a configuration where the third lumen is used for continuous gravity irrigation.

FIG. 6 shows an embodiment of the present invention in which components for continuous filling of the bladder with irrigation fluid that was illustrated in FIG. 3 are combined with the hand irrigation system using a 3-port 3-position (3-phase) syringe that was illustrated in FIG. 4. This allows the embodiment shown in FIG. 6 to be used for gravity irrigation, but not drainage (part of the functions of the system shown in FIG. 3), for manual irrigation and drainage (all of the functions of the system shown in FIG. 4) without disconnecting any line. It does not allow the system to be used for continuous drainage.

Referring to FIG. 6, the components used for continuous filling of the bladder that were illustrated at 340, 342, and 344 in FIG. 3 serve the same functions in the configuration shown in FIG. 6. The system 600 in FIG. 6 can fit the same bladder 90 in the same patient 80 as the systems shown previously. The system 600 in FIG. 6 uses a three-lumen urinary catheter 310 instead of the two-lumen urinary catheter (110 in FIG. 4). In the configuration shown at 600, the input fluid lumen 320 can be used to continuously fill the bladder with irrigation fluid, just like was done in FIG. 3. An input clamp valve 344 can be used to clamp the input fluid line 342 when the input (or irrigation) fluid source 340 needs to be changed or the bladder is too full. The system shown in FIG. 6 uses the same type of balloon inflation lumen 110, urinary catheter balloon 112, balloon inflation port 114, and balloon inflation valve 116 that were shown previously. The other components in the system shown in FIG. 6 are the same as the like numbered components in the system shown in FIG. 4. It should be noted that the embodiment shown at 600 in FIG. 6 comprises two input fluid sources 340, two input fluid lines 342, and two input line clamps 344, with one set connected directly to the catheter 310 and the second set connected to the input port of the 3-port 3-position syringe 410. The set connected to the input port of the 3-port 3-position syringe can also comprise the optional check valve 346 that was previously shown with reference to FIG. 4.

Figure 7:
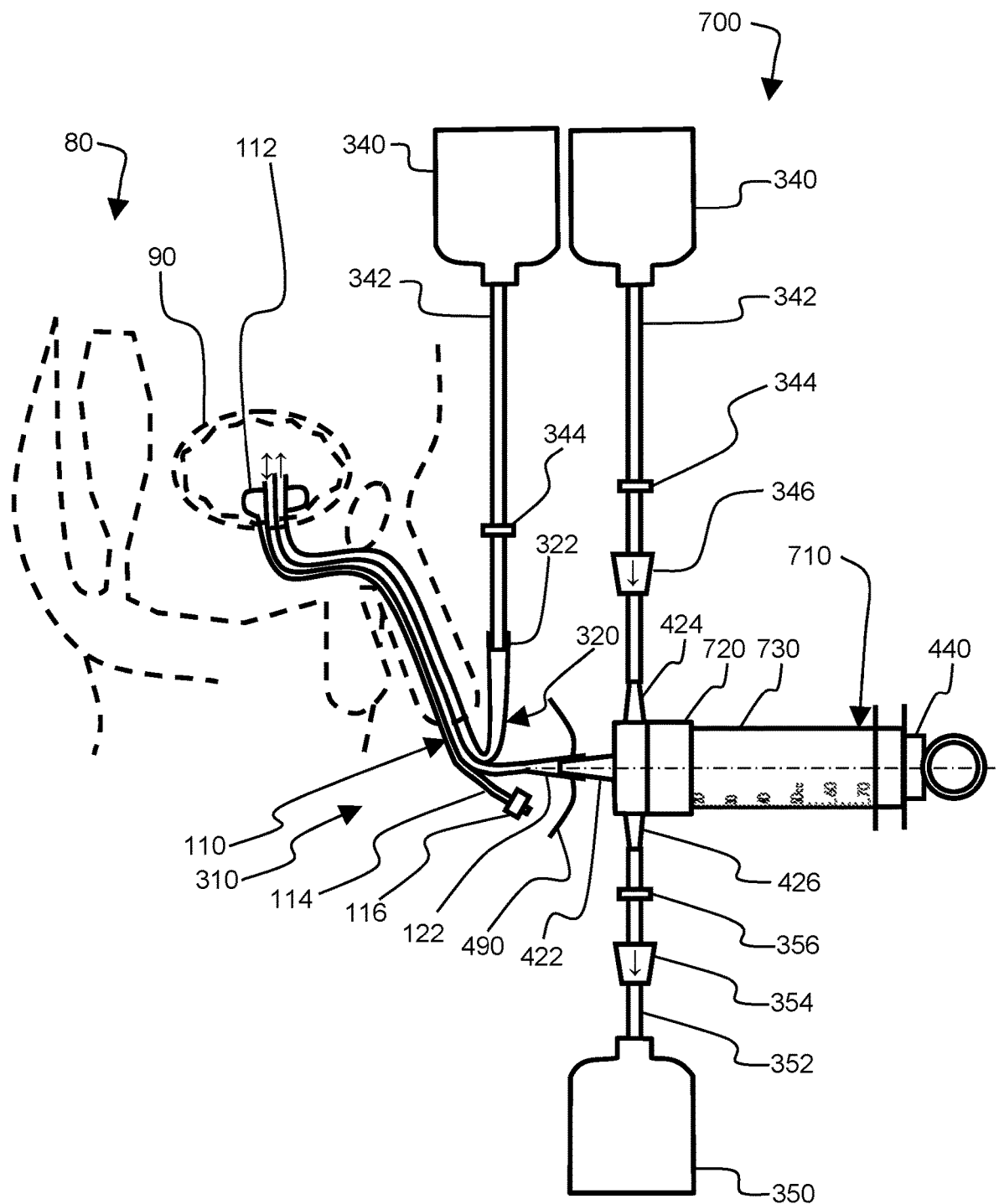
FIG. 7 shows a closed system that uses a 3-port 4-position syringe that combines all of the functions shown in FIG. 3 with the functions shown in FIG. 4 for a total of four operational phases.

FIG. 7 shows another embodiment of the present invention. In the embodiment shown at 700, the functions of the embodiment that was illustrated in FIG. 4 are combined with all of the functions of the continuous gravity irrigation and drainage system shown in FIG. 3 to create a single system that can perform all of the functions of these two systems without the need to connect or disconnect any ports or lines. In the embodiment shown at 700 in FIG. 7, this combination of all functions is accomplished by replacing the three-port three-position syringe of FIG. 3 with a three-port four-position syringe that is shown at 710 in FIG. 8. This four-position syringe 710 differs from the three-position syringe, 410 in FIG. 4, by having a four-position port body 720, and a four-position barrel 730. The fourth position of this syringe 710 is used to configure the system so that the catheter port 422 is connected to the drainage port 426 and that fluid can continuously drain from the bladder 90 of the patient 80 into the drainage vessel 130 without any hand pumping. All other components and features of the system 700 shown in FIG. 7 are the same as the equivalently numbered components and features that were illustrated in previous figures.

Figure 8:
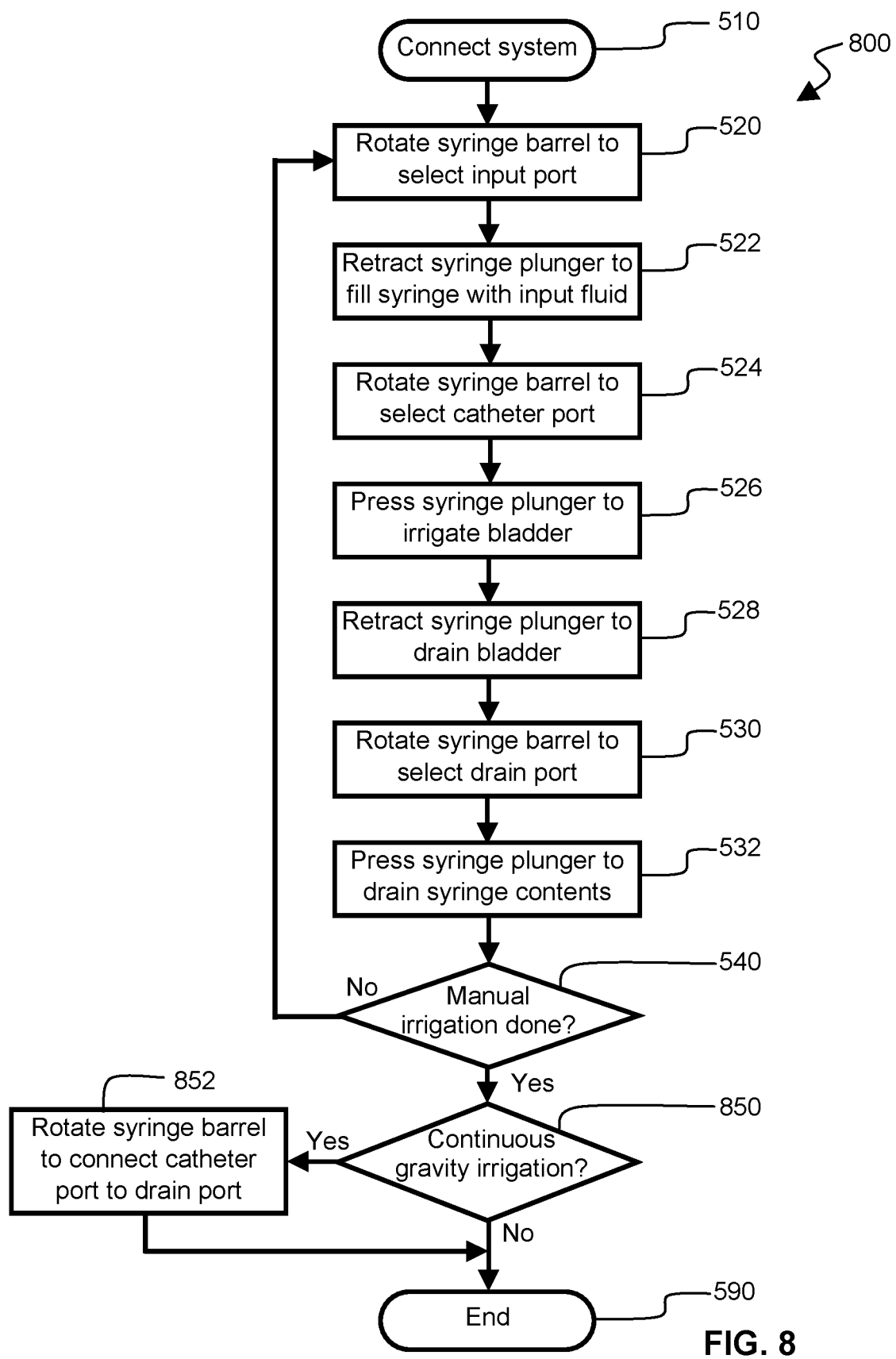
FIG. 8 provides a flowchart of a method for using the system illustrated in FIG. 7.

The system shown in FIG. 7 can be operated by using the manual irrigation process shown in FIG. 8. This process is similar to the process shown in FIG. 5 in that steps 510 to 540 and 590 are similar. Once hand irrigation is done, the operator of the system shown in FIG. 7 can choose, at step 850, to provide continuous gravity drainage, by rotating the syringe barrel to a position that connects the catheter port (422 in FIG. 7) to the drainage port (426 in FIG. 7), a step shown at 852. Connecting the catheter port (422 in FIG. 7) to the drainage port (426 in FIG. 7), in the four-position syringe (710 in FIG. 7) allows continuous drainage to occur at the same time as continuous irrigation is occurring in the embodiment illustrated in FIG. 7.

Figure 9:
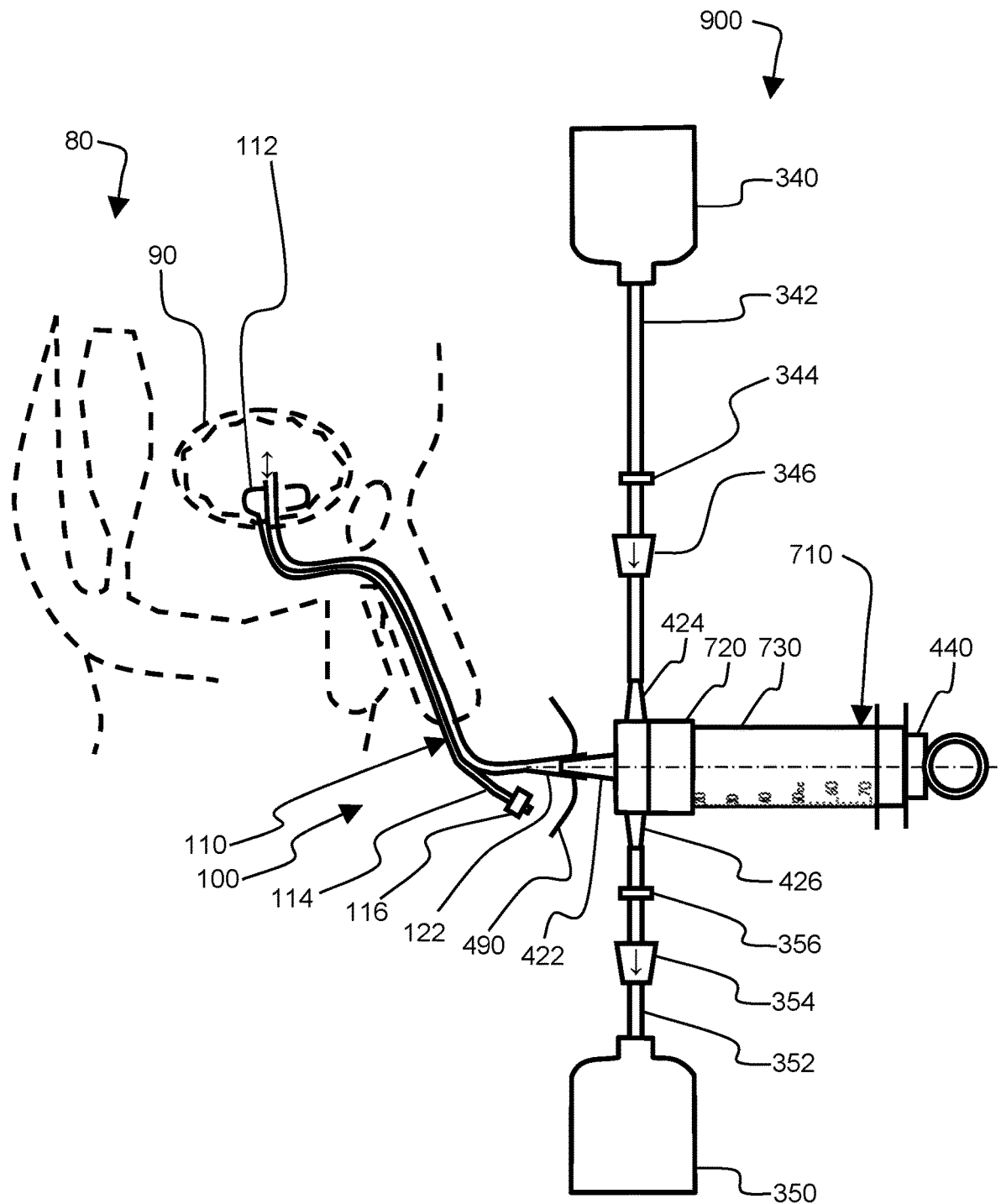
FIG. 9 shows a manual irrigation and drainage system comprising a 3-port 4-position syringe and a two-lumen urinary catheter that has four operational phases.

FIG. 9 shows another embodiment of the present invention. The embodiment shown at 900 includes all of the functions of the embodiment shown in FIG. 7, except that:
(a) The three-lumen urinary catheter in FIG. 7 has been replaced with a two-lumen catheter, shown at 100; and
(b) The second input fluid source, 340 in FIG. 7, and related input fluid line 320 and input line clamp 344 are not part of the system shown at 900 in FIG. 9.

The system shown at 900 in FIG. 9 is a single system that can perform a continuous gravity drainage function (or phase) along with the three other all of the functions (or phases) of the system that was illustrated with reference to FIG. 4, by substituting the 3-port 4-position syringe, 710 in FIG. 7, for the 3-port 3-position syringe, 410 in FIG. 4. The system of FIG. 9 can change from a manual irrigation to continuous drainage without the need to connect or disconnect any ports or lines. The four-position syringe 710 differs from the three-position syringe, 410 in FIG. 4, by having a four-position port body 720, and a four-position barrel 730. The fourth position of this syringe 710 is used to configure the system so that the catheter port 422 is connected to the drainage port 426 and that fluid can continuously drain from the bladder 90 of the patient 80 into the drainage vessel 130 without any hand pumping. All other components and features of the system 900 shown in FIG. 9 are the same as the equivalently numbered components and features that were illustrated in previous figures.

The following table further clarifies the functionality differences between the embodiments shown in FIG. 3, FIG. 4, FIG. 6, FIG. 7, and FIG. 9:

|  | FIG. 3 (Prior Art) | FIG. 4 3 phases | FIG. 6 3 phases | FIG. 7 4 phases | FIG. 9 4 phases |
| --- | --- | --- | --- | --- | --- |
| Closed manual filling of syringe | No | Selectable first phase | Selectable first phase | Selectable first phase | Selectable first phase |
| Closed manual bladder filling and extraction | No | Selectable second phase | Selectable second phase | Selectable second phase | Selectable second phase |
| Closed manual drainage of syringe | No | Selectable third phase | Selectable third phase | Selectable third phase | Selectable third phase |
| Continuous gravity filling of bladder? | Yes | No | Yes | Yes | No |
| Continuous gravity drainage of bladder? | Yes | No | No | Selectable fourth phase | Selectable fourth phase |
| Syringe ports | No syringe | 3 | 3 | 3 | 3 |
| Syringe positions | No syringe | 3 | 3 | At least 4 | At least 4 |
| Catheter lumens | 3 | 2 | 3 | 3 | 2 |

Here is an additional description of some differences between the prior art (FIG. 1A, FIG. 1B, FIG. 2, and FIG. 3) and embodiments of the present invention (FIG. 4, FIG. 5, FIG. 6, FIG. 7, FIG. 8, and FIG. 9):
(a) The prior art is systems and methods for manual irrigation and/or gravity filling and drainage that require the system to be opened. Embodiments of the present invention are closed systems and methods for manual irrigation, that can also include a fourth phase for gravity drainage. This fourth phase could be implemented using a fourth selectable syringe position and this fourth syringe position could be selected without needing to open the system.
(b) The prior art illustrated in FIG. 3 does not include any manual irrigation or any syringe.
(c) The three syringe ports in the systems of FIG. 4, FIG. 6, FIG. 7, and FIG. 9 connect to an input fluid source (340 in FIG. 4, FIG. 6, FIG. 7, and FIG. 7, which is also called the "Fill" port), a catheter (100 in FIG. 4 and FIG. 9, or 310 in FIG. 6 and FIG. 7), and a drainage vessel (350 in FIG. 4, FIG. 6, FIG. 7, and FIG. 9).

4. Detailed Description of a 3-Port 3-Position Syringe Embodiment

Figure 10A:
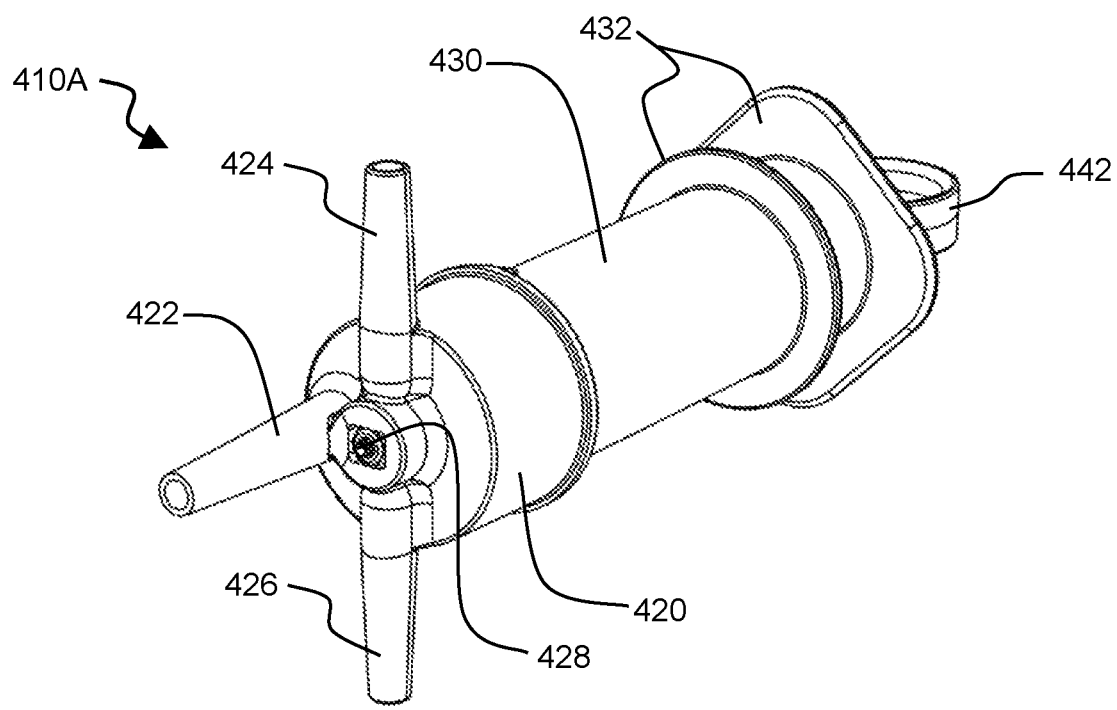
FIG. 10A shows an isometric view of an example of a 3-port 3-position syringe comprising three axial ports in which the positions are chosen by rotating the barrel relative to the port body.
Figure 10B:
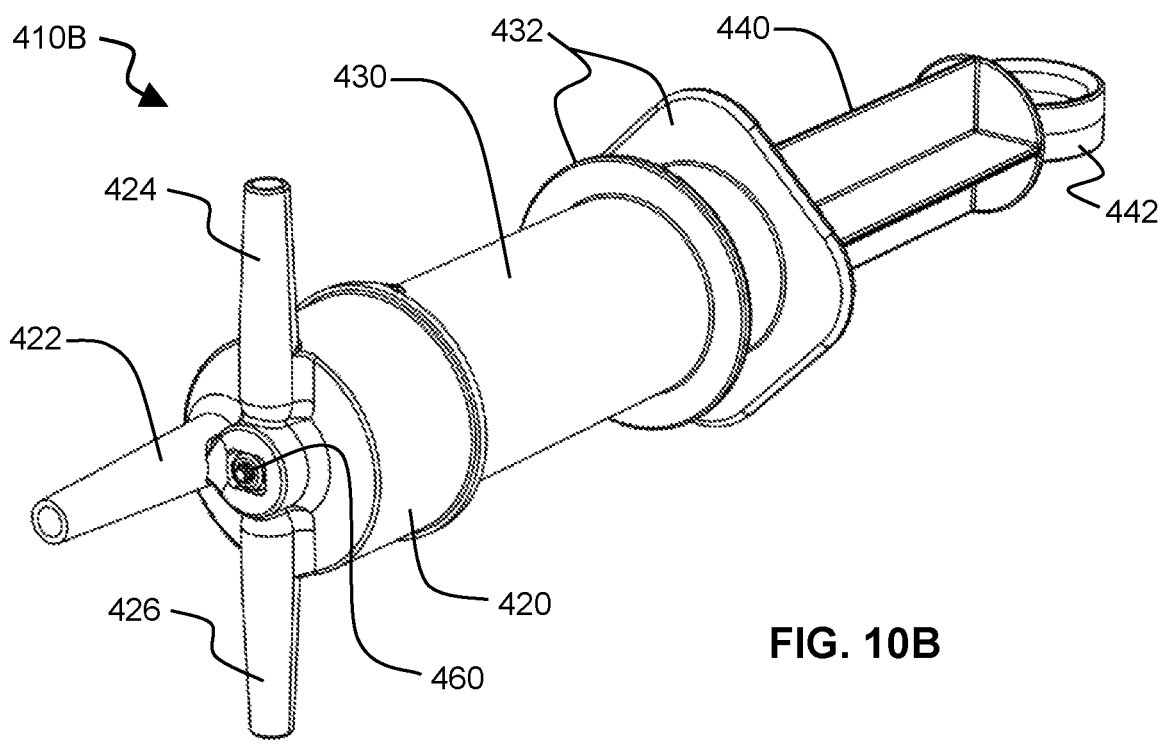
FIG. 10B shows the syringe of FIG. 10A in its extended position.

FIG. 10A and FIG. 10B are isometric views of the three-port three-position syringe that was shown at 410 in FIG. 4 and FIG. 6. FIG. 10A shows the syringe at position 410A with the plunger 440 inserted completely in the barrel 430 to minimize the volume of fluid in the barrel 430. FIG. 10B shows the syringe at position 410B with the plunger 440 extended out of the barrel 430 to maximize the volume of fluid in the barrel 430. The port body 420 comprises three ports: the input port 424; the catheter port 422; and the drainage port 426. Also shown is a port body fastener 460 which connects the port body 420 to the barrel 430 while allowing the barrel to rotate relative to the port body. Also shown in FIG. 10A and FIG. 10B is a barrel grasping feature (or features), shown at 432, and a plunger grasping feature, shown at 442, that that facilitate manual axial movement of the plunger 440 inside the barrel 430. In the embodiment shown, the barrel grasping feature 432 comprises two regions of the barrel that stick out from the outside of the barrel cylinder to provide a place configured for placement of one or more fingers. The plunger grasping feature 442 is a ring through which a user could place a finger. These features 432 and 442 could be any shapes capable of being understood by anyone skilled in the art.

Figure 11:
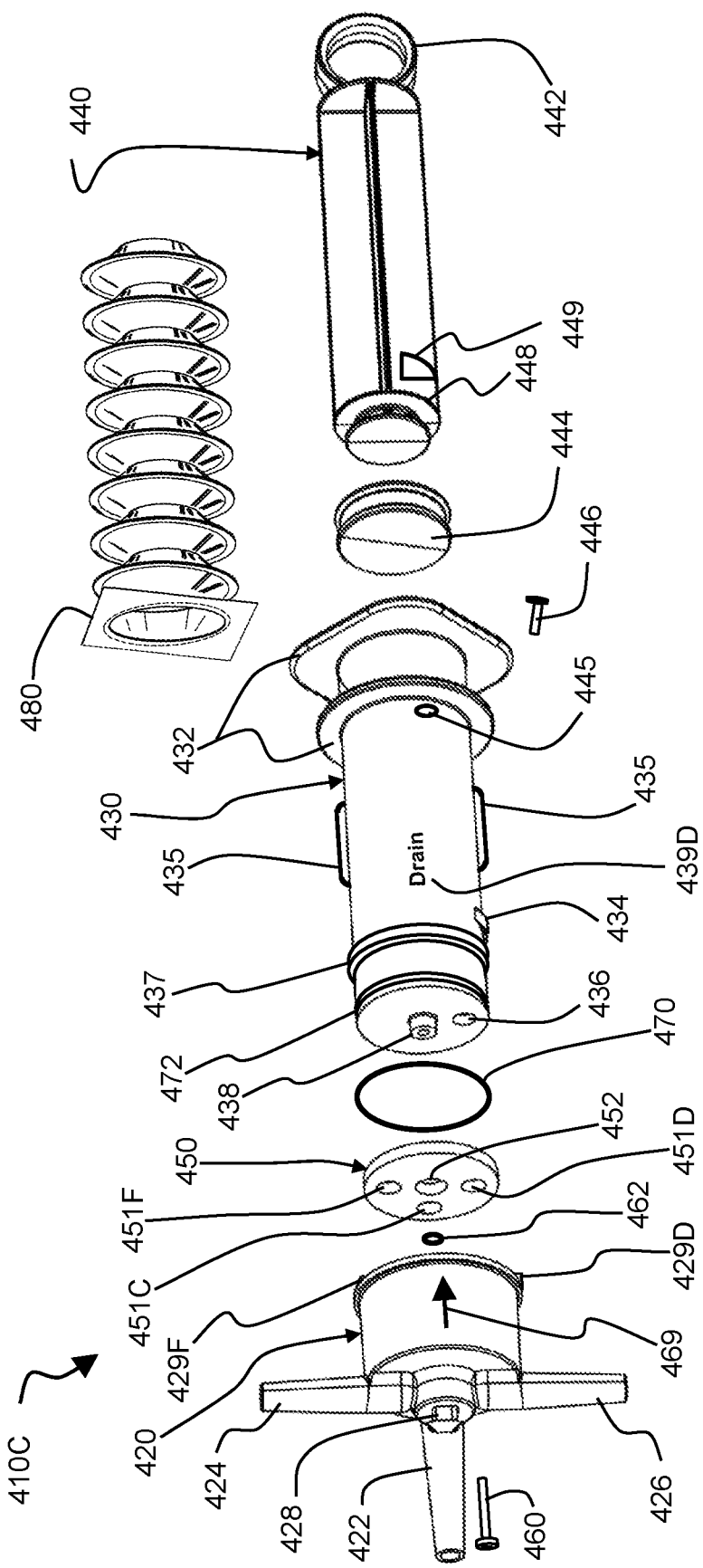
FIG. 11 shows an exploded view of the syringe of FIG. 10A and FIG. 10B along with some additional components and features.

FIG. 11 is an exploded view of the syringe 410C that was shown at 410 in FIG. 4 and FIG. 6, at 410A in FIG. 10A, and at 410B in FIG. 10B and shows some further components and features as well. Some of the main components in this exploded view of the syringe 410C include:

(a) The port body 420 comprising the input port 424, catheter port 422, and drainage port 426;

(b) A gasket 450 that seals the port body 420 and barrel 430;

(c) A port body fastener 428 to secure the port body 420 to the barrel 430;

(d) The barrel 430, further comprising a barrel indexing feature 434, a barrel port (or aperture) 436, a cylindrical attachment boss 438, and the barrel grasping features 432;

(e) A plunger seal, shown at 444; and (f) The plunger 440, which includes the plunger grasping feature 442.

The barrel 430 in FIG. 11 comprises a hollow cylinder with an open end and a closed end. The closed end of the barrel 430 is configured to fit inside the cup-shaped port body 420, with the gasket 450 sitting between the exterior of the closed end of the barrel and the circular bottom of the cup-shaped port body 420. The barrel port 436 is a circular axial aperture in the closed end of the cylindrical barrel 430 configured for transmission of fluid between the interior of the barrel and the ports (422, 424, and 426) in the port body that each have circular apertures in the circular bottom of the cup-shaped port body at one end of the ports (422, 424, and 426). The opposite ends of each of the three ports (422, 424, and 426) are configured for attachment to a catheter (for the catheter port 422), a fill line (for the fill port 424), and a drainage line (for the drainage port 426). Rotation of the barrel 430 relative to port body 420 allows for selective and exclusive transmission of fluid between the interior of the barrel 430 and one of the three ports the port body: the input (or fill) port 424; the catheter port 422; or the drainage port 426.

The gasket 450 in FIG. 11 is configured for rotational alignment with the port body 420 to seal the fluid connection between the ends of one of the three ports (422, 424, or 426) on the port body 420 and the barrel port 436. The gasket 450 would typically be made of a medical grade elastomer. In the configuration shown, the gasket 450 is a flat circular disk with three fluid flow apertures (451F, 451C, and 451D) surrounding a central mounting aperture 450. All four gasket apertures (451F, 451C, 451D, and 452) are circular. All four gasket apertures go through the gasket 450 in an axial direction (i.e. through the circular disk). The three fluid flow apertures (451F, 451C, and 451D) are equidistant from the central mounting aperture 452 and this distance is the same as the distance between the center of the barrel attachment boss 438 and the barrel port 436. In the configuration shown in FIG. 11, the three fluid flow apertures in the gasket (451F, 451C, and 451D) are spaced 90 degrees apart. When assembled, the three fluid flow apertures align with the respective circular apertures in the following configuration:

(a) The fill aperture 451F aligns with the barrel port 436 and the end of the fill port 424 for fluid transmission in an axial direction when the barrel is rotated into a first position;

(b) The catheter aperture 451C aligns with the barrel port 436 and the end of the catheter port 422 for fluid transmission in an axial direction when the barrel is rotated into a second position; and (c) The drainage aperture 451D aligns with the barrel port 436 and the end of the drainage port 426 for fluid transmission in an axial direction when the barrel is rotated into a third position.

When assembled, the barrel attachment boss 438 fits into the gasket central circular aperture 452. The port body fastener 460 attaches the port body 420 to the barrel 430 by going through a central aperture in the port body 428, through the gasket central circular aperture 452, and through the barrel attachment boss 438. A fastener O-ring 462 ensures that fluid cannot leak from the region surrounding the port body fastener 460 and the exact location of this fastener O-ring will be shown and explained with reference to FIG. 15B. The barrel attachment boss 438 is a raised cylindrical section in the center of the circular closed end of the barrel 430 that facilitates the alignment of the barrel 430, port body 420, and gasket 450. The port body fastener 460 can be any mechanical fastener device, system or method capable of being understood by anyone skilled in the art. In FIG. 11 the port body fastener 460 has been shown as a machine screw. The port body fastener 460, port body 420, barrel 430, and gasket 450 are configured so that the port body 420 can be freely rotated about the axis of the barrel 430, but the port body 420 is prevented from moving axially relative to the barrel 430. The gasket 450 and port body 420 also comprise a rotational alignment feature configured to ensure that gasket 450 rotates with the port body 420 and not with the barrel 430, when the barrel 430 is rotated inside the port body 420.

Further referring to FIG. 11, the barrel indexing feature 434 is a raised area on the outside of the cylindrical barrel that is configured for assisting in the rotational alignment of the barrel port 436 with one of the three ports in the port body (422, 424, or 426) by aligning with port body indexing features 429F, 429C, and 429D on the port body 420 that will be further detailed and described with reference to FIG. 13A, FIG. 13B, FIG. 14A, FIG. 14B, FIG. 15A, and FIG. 16. The fill indexing feature 429F and drainage indexing feature 429D are two of these features and are visible in FIG. 11. When the fill indexing feature (429F in FIG. 11, FIG. 13B, FIG. 14A, FIG. 14B, FIG. 15A, and FIG. 16) is aligned with the barrel indexing feature 434, the system is configured for exclusive transmission of fluid from the input (or fill) port 424 to the interior of the barrel. When the catheter indexing feature (429C in FIG. 13A, FIG. 13B, FIG. 14A, and FIG. 14B) is aligned with the barrel indexing feature 434, the system is configured for exclusive transmission of fluid between the interior of the barrel and the catheter port 422. When the drainage indexing feature (429D in FIG. 11, FIG. 13B, FIG. FIG. 14A, FIG. 14B, and FIG. 15A) is aligned with the barrel indexing feature 434, the system is configured for exclusive transmission of fluid from the interior of the barrel to the drainage port 426.

The plunger 440 in FIG. 11 is configured for insertion into the open end of the hollow cylindrical barrel 430 and for axial travel inside the hollow cylindrical barrel 430 to increase and decrease the quantify of a fluid in a cylindrical barrel volume defined by the barrel hollow cylinder, the barrel closed end, and the sealed end of the plunger 444. The circular plunger seal 444 is typically an elastomeric cap on the end of the plunger 440. The plunger seal 444 is designed to help prevent fluid from escaping from the barrel 430 when the plunger 440 is pressed into the barrel 430 and to help prevent air from entering the barrel 430 when the plunger 440 is retracted from the barrel 430. The plunger grasping feature (or grip) 442 is designed to assist with manual grasping of the plunger and axial movement of the plunger inside of the barrel 430. This grip 442 is located on the end of the plunger that is opposite of the plunger seal 444.

FIG. 11 also illustrates that the barrel of the multiport syringe can have an element, feature or features to restrict the travel (or axial movement) of the plunger in the barrel. This device, feature or features could be configured to prevent the plunger from exiting the barrel. This feature or features could be configured to lock the plunger in a partially extended position to allow for communication between the catheter and the drain ports for continuous gravity drainage. The plunger travel-limiting element, feature, or features could be mounted on the barrel, on the plunger, and/or on another component in the multi-port syringe. Plunger travel could be limited using a feature or features on more than one part of the syringe. In the embodiment shown in FIG. 11, plunger axial travel can be constrained by a plunger stop pin 446, that is designed to be inserted into a plunger stop pin hole 445 in the cylindrical wall of the barrel 430. When the plunger stop pin 446 is inserted into the plunger stop hole 445 and the plunger 440 is rotated so the plunger stop pin 446 is between a plunger end rib 448 and a plunger stop pin rib 449 on the plunger 440, axial travel of the plunger 440 in the barrel 430 is limited by the plunger end rib 448 and the plunger stop pin rib 449. Typically, the plunger stop pin 446 is permanently installed and locking the travel of the plunger 440 is accomplished by sliding the plunger past the stop pin in the slot next to the plunger stop in rib 449.

Embodiments of the syringe (410 in FIG. 4 and FIG. 6, 710 in FIG. 7 and FIG. 9, 410A in FIG. 10A, 410B in FIG. 10B, and 410C in FIG. 11) can be configured for attachment to a patient for an extended period of time when repeated intermittent manual irrigation as shown in FIG. 5 is needed over a prolonged hospitalization. In one embodiment, the syringe 410C in FIG. 11, could have one or more barrel attachment features, shown at 435. The barrel attachment feature(s) 435 could be located on the outside of the cylindrical barrel 430. The barrel attachment feature(s) 435 could be configured as loops with a slotted opening that accept a strap. The barrel attachment feature(s) 435 could be parallel bars on each side of the barrel 430 located 180 degrees of each other and would sit at 90 degrees from the front of the barrel when it is in the continuous gravity drain phase as noted by FIG. 19 and FIG. 20. The barrel attachment feature(s) 435 could be made of the same or similar material to the barrel 430. The barrel attachment feature(s) 435 could extend a few millimeters from the body of the barrel. The barrel attachment features(s) 435 could be a few centimeters in length and located between open end of the barrel and the rim of the port body. Therefore, once manual irrigation is no longer needed the multiport syringe could be placed into continuous gravity drainage mode and then strapping the syringe to the patient by threading a strap through the barrel attachments feature(s) 435 taking the forward-facing strap extension and placing this strap through one barrel attachment feature 435, then around the body of the barrel 430 and then through the opposite positioned strap before being attached again to the leg strap that is wrapped around the patient's leg. The syringe could also be stabilized with only one barrel attachment feature 435 being strapped as well.

The barrel 430 could have a seal or cover at the open end of the barrel that attaches or wraps circumferentially around the plunger's shaft. This prevents the introduction of outside contaminants into the system and reduces the risk of bodily fluids getting on the patient or user. In FIG. 11, a plunger cover 480 that comprises a bellows is shown as one example of such a seal or cover. One end of this plunger cover 480 could be attached to the barrel grasping feature 432. The other end of the plunger cover 480 could be attached to the plunger grasping feature 442. The plunger cover 480 could also be a flexible member, such as a balloon, that wraps around the entire exposed end of the plunger 440, including the grip 442.

Figure 12:
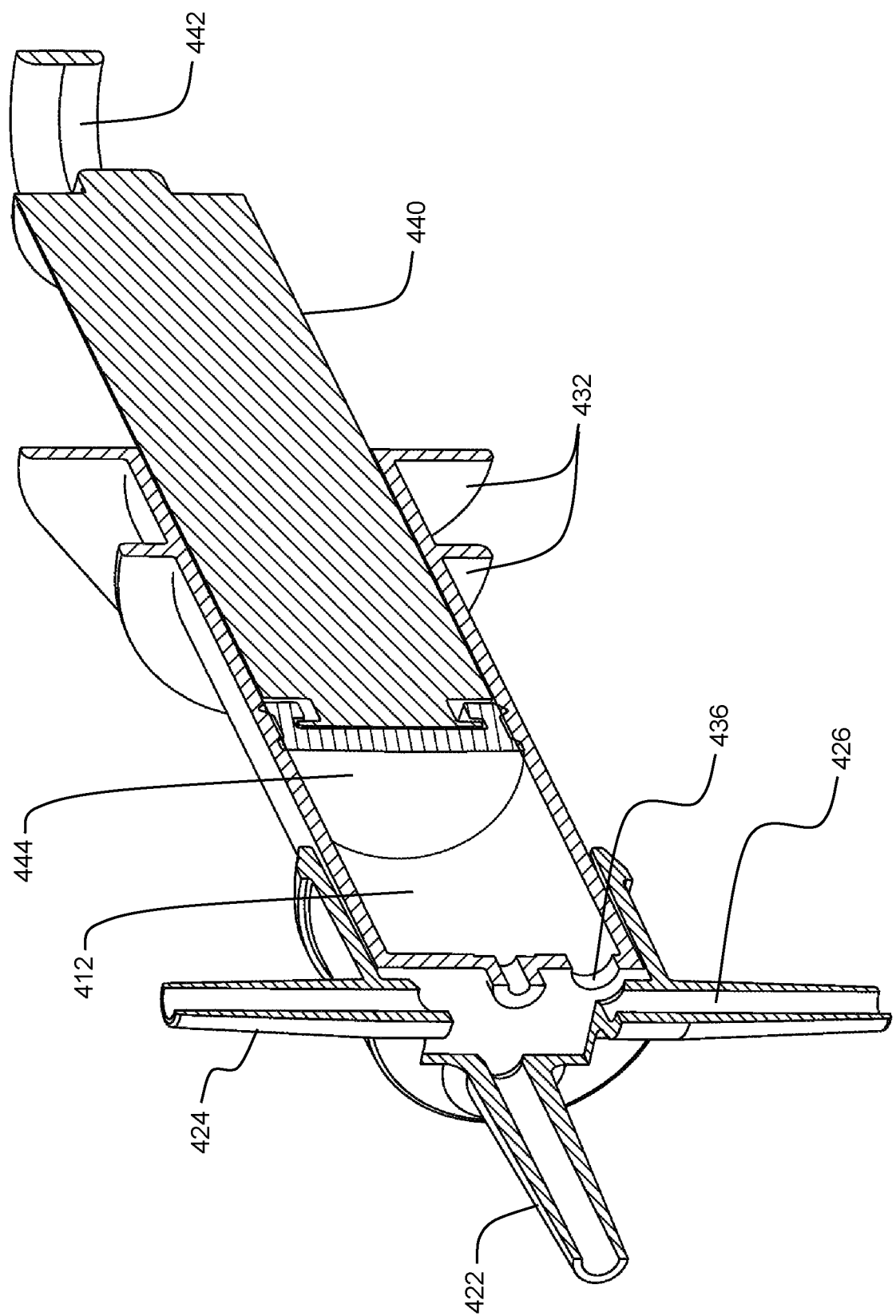
FIG. 12 shows a section view of the syringe of FIG. 10A, FIG. 10B, and FIG. 11.

FIG. 12 shows a section view of the syringe of FIG. 10A, FIG. 10B, and FIG. 11, and illustrates the syringe cavity 412 that expands and contracts as the syringe plunger 440 is inserted and retracted. Worth noting are the plunger cap 444, the barrel port 436 that is aligned with the drainage port 426, the barrel grasping features 432, and the plunger grasping feature 442. For simplicity the gasket and port body fastener that were illustrated in FIG. 11 are not included in FIG. 12.

Figure 13A:
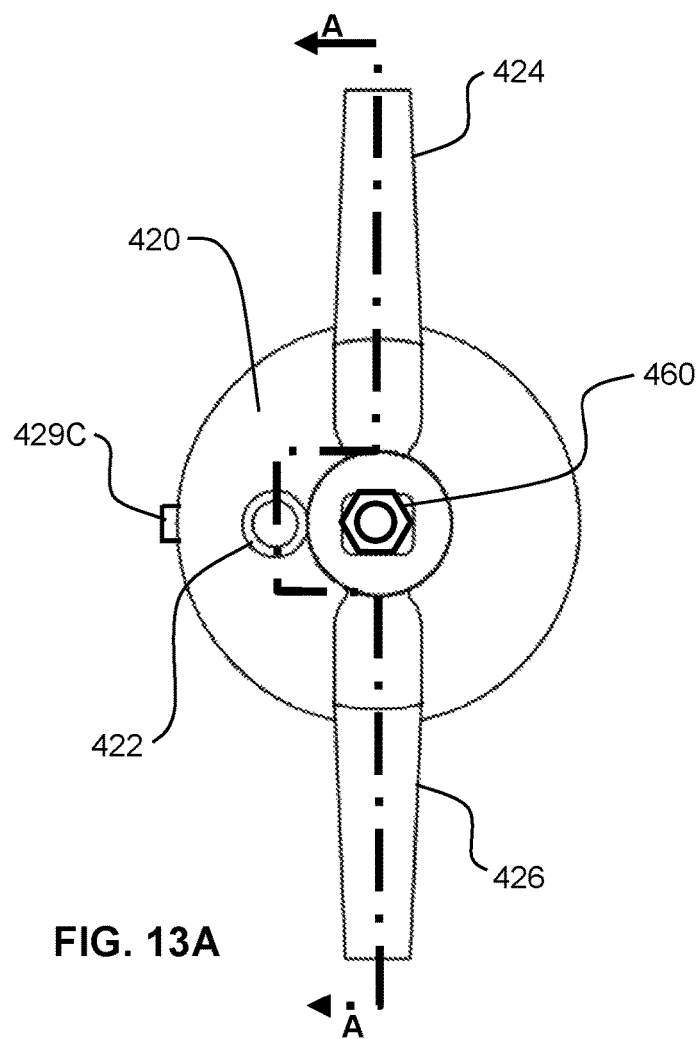
FIG. 13A shows an end view of the port body of the syringe of FIG. 10A, FIG. 10B, FIG. 11, and FIG. 12.

FIG. 13A shows an end view of the port body 420 of the syringe of FIG. 10A, FIG. 10B, FIG. 11, and FIG. 12 to help illustrate the relative positions of the input port 424, catheter port 422, and drainage port 426. Also shown is the port body fastener 460.

Figure 13B:
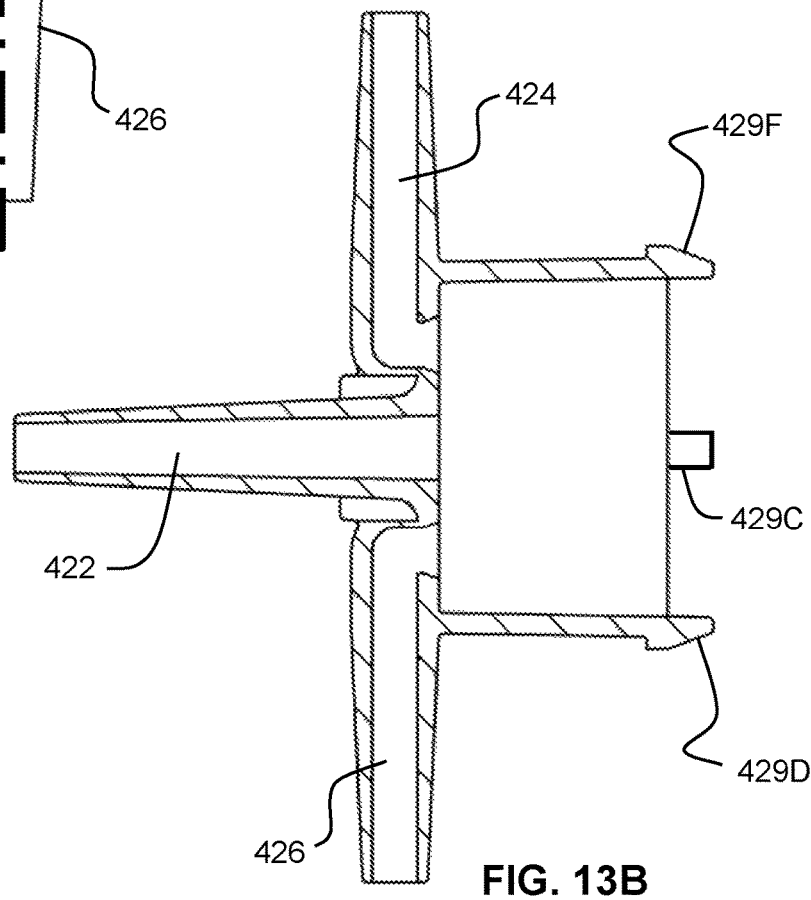
FIG. 13B shows section A-A of the port body of FIG. 13A.

FIG. 13B shows section A-A of the port body 420 and the positions of the input port, catheter port 422 and drainage port 426. This also shows three port body indexing features 429F (indexing feature for input or fill port), 429C (indexing feature for catheter port), and 429D (indexing feature for drainage port). The indexing feature for the catheter port 429C is also shown in FIG. 13A.

Figure 14A:
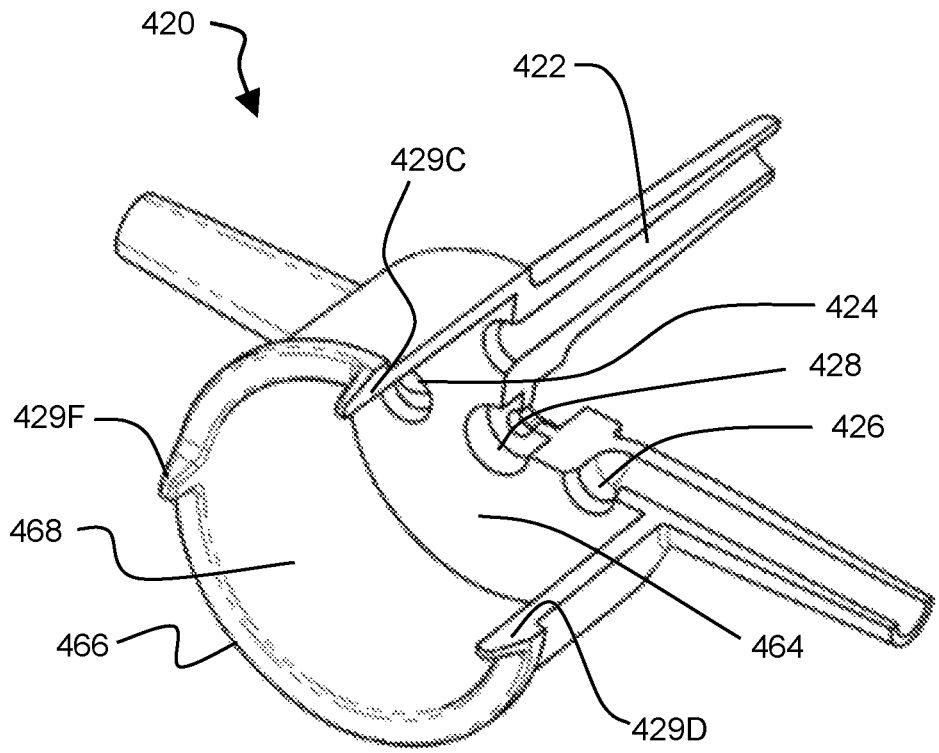
FIG. 14A and FIG. 14B show two additional section views of the port body of FIG. 13A and FIG. 13B.
Figure 14B:
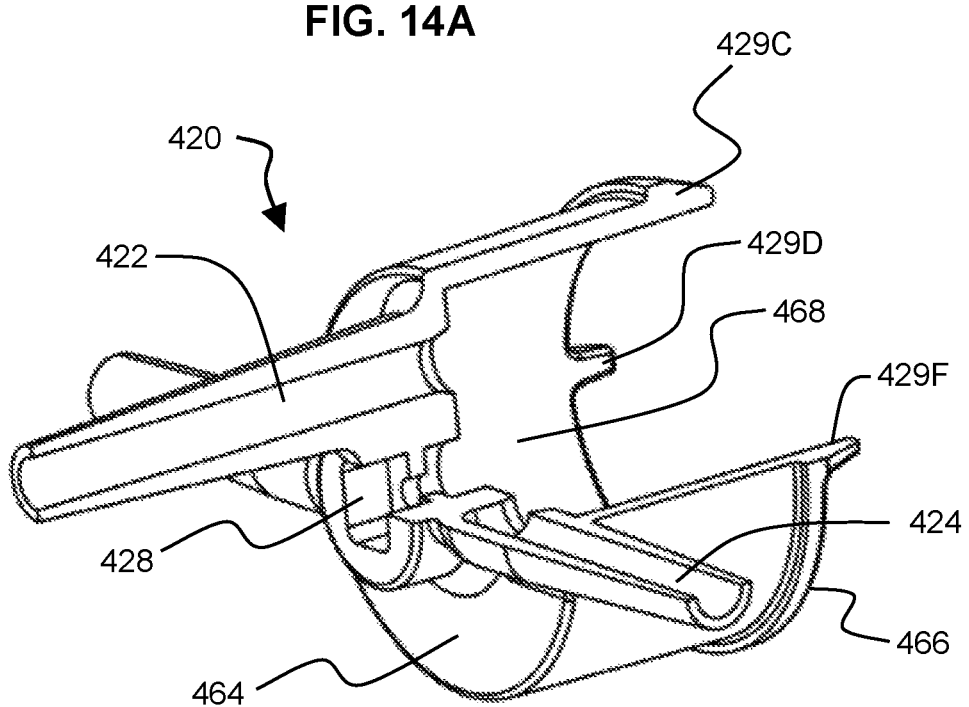

FIG. 14A and FIG. 14B show two additional section views of the port body 420 of FIG. 13A and FIG. 13B that more clearly illustrate details. As shown in FIG. 14A and FIG. 14B, the port body 420 comprises a cylindrical cup, which consists of a circular bottom 464, a rim (or lip) 466, and a cylindrical wall 468 separating the circular bottom 464 from the rim 466. Located on the rim 466 are a minimum of three port body rotational indexing features: one for the input or fill port 429F, one for the catheter port 429C, and one for the drainage port 429D. In the embodiment shown in FIG. 14A and FIG. 14B, the port body indexing features (429F, 429C, and 429D) protrude axially from the rim on a side of the rim opposite of the port body cylindrical wall 468. Also illustrated in FIG. 14A are four circular axial apertures in the port body circular bottom: one for the input or fill port 424, one for the catheter port 422, one for the drainage port 426, and an aperture in the center of center port body circular bottom. The apertures for the fill, catheter, and drainage ports are designed to align with the barrel port (436 in FIG. 11) when the barrel is rotated to align with one of the port body rotational indexing features (429F, 429C, or 429D) for exclusive fluid transmission between the interior of the barrel (430 in FIG. 11) and one of the ports (422, 424, or 426). The central port body circular bottom aperture 428 can be used for alignment with the barrel (430 in FIG. 11) when the syringe is assembled. The central port body circular bottom aperture 428 can also be used by a port body fastener (460 in FIG. 11) that connects the port body to the barrel (430 in FIG. 11).

Figure 15A:
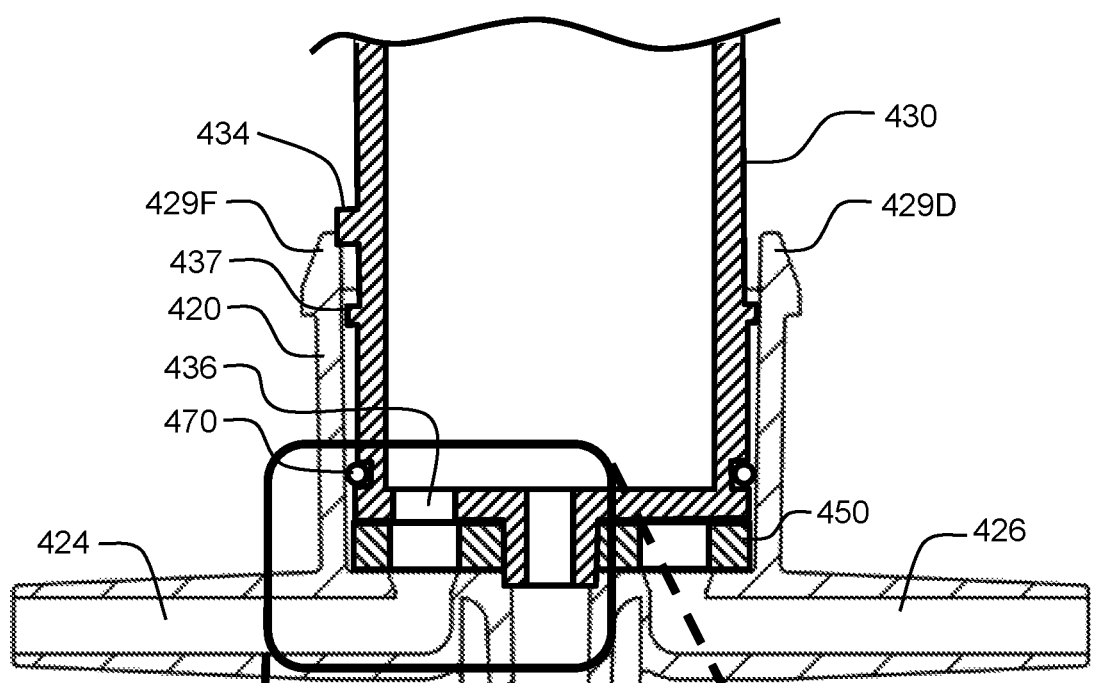
FIG. 15A shows the sectioned port body of FIG. 13B with the sectioned barrel of FIG. 12 and sectioned gasket that was shown in FIG. 11.
Figure 15B:
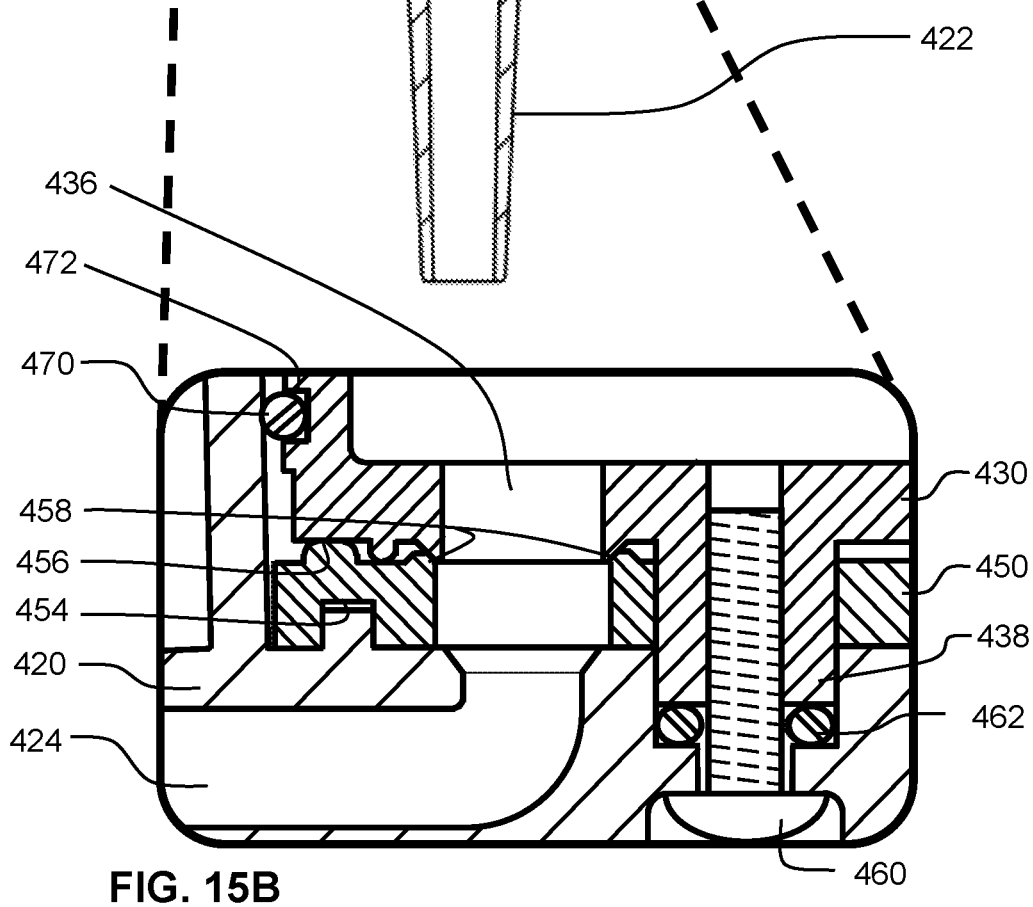
FIG. 15B shows further details of one part of FIG. 15A.

FIG. 15A shows the sectioned port body 420 of FIG. 13B with the sectioned barrel 430 of FIG. 12 and sectioned gasket 450 that was shown in FIG. 11. FIG. 15B shows further details of one part of FIG. 15A. The section shown in FIG. 15A has been stepped in the center to illustrate the sectioned catheter port 422. The view in FIG. 15B is taken straight across the center of the port body, and also shows the port body fastener 460.

Referring to FIG. 15A and FIG. 15B, the port body is shown at 420 and the barrel is shown at 430. The port body 420 comprises the input port 424 and FIG. 15A also shows the drainage port 426, the fill port indexing feature 429F and the drainage port indexing feature 429D. In this view, the fill port indexing feature 429F is rotationally aligned and engaged with the barrel indexing feature 434, which means that the barrel port 436 is rotationally aligned with the fill port 424. This rotation of the barrel port 436 and the fill port 424 is also shown in FIG. 15B.

FIG. 15A and FIG. 11 also show a barrel axial alignment feature 437. The barrel axial alignment feature 437 is a circular ring around the barrel hollow cylinder that provides for a tight fit between the port body 420 and the barrel 430 in a region close to the lip of the cup-shaped port body 420. The barrel axial alignment feature 437 improves the axial alignment of the barrel 430 in the port body 420. The barrel axial alignment feature 437 is near the port body rim (or lip) when the medical syringe system is assembled.

Another point of engagement between the port body and the barrel is a barrel O-ring seal 470 shown in FIG. 15A, FIG. 15B, and FIG. 11. The barrel O-ring seal 470 is located between the cylindrical wall of the port body cup and the outside of the cylindrical body of the barrel 430 in a region close to the closed end of the barrel 430. In the embodiment shown in FIG. 15A, FIG. 15B, and FIG. 11, the O-ring seal fits into a barrel O-ring groove 472 that is a circular groove in the cylindrical body of the barrel 430. The barrel O-ring seal 470 also improves the axial alignment of the barrel 430 in the port body 420. The barrel O-ring seal 470 is one of the seals that prevents the escape (or leakage) of fluids from the interior of the hollow cylindrical barrel 430 (i.e. preventing the leakage of fluid between the cup-shaped region of the port body 420 and the barrel 430).

Further referring to FIG. 15A and FIG. 15B, the gasket 450 provides a seal between the closed end of the barrel 430 and the circular bottom of the port body 420. In one embodiment, the gasket 450 rotates with the port body 420, and therefore has the same three circular apertures that axially align with the ports (422, 424, and 426) in the circular bottom of the port body. It is also possible to have a gasket 450 that rotates with the barrel 430 and would therefore have only one aperture that would stay aligned with the barrel port 436. As shown in FIG. 15B, the gasket can have a variety of sealing and alignment grooves and ridges such as the gasket circular alignment groove shown at 454, the gasket circular alignment ridge shown at 456, and the gasket port sealing ring shown at 458. These ridges and grooves can align and seal against mating features in the port body 420 and barrel 430.

FIG. 15B also shows that the barrel attachment boss 438 goes through the gasket central aperture (452 in FIG. 11) and that there is a fastener O-ring 462 that sits in a pocket between the port body 420 and the barrel attachment boss, 438 in FIG. 11, and around the port body fastener 460.

Figure 16:
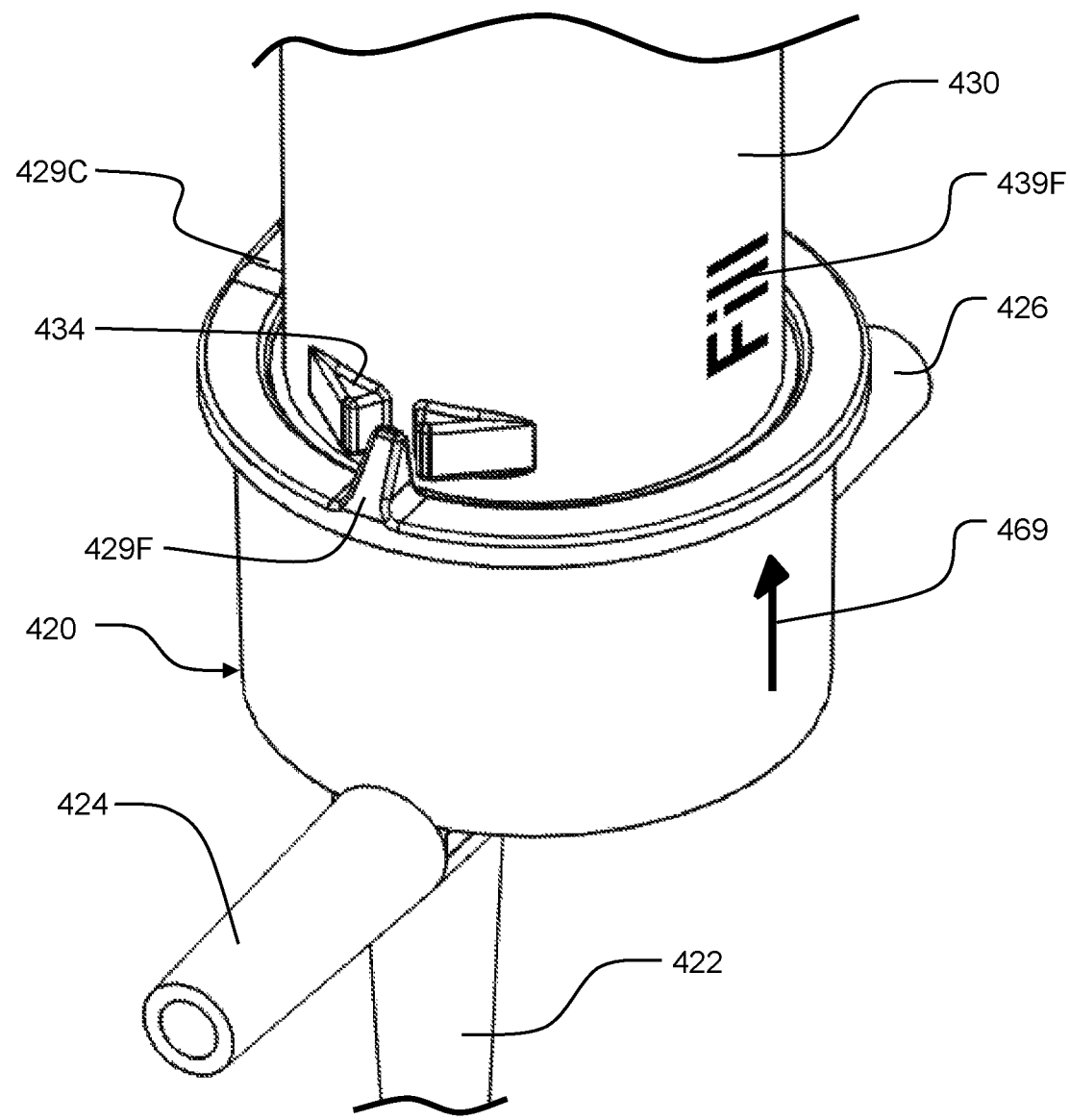
FIG. 16 shows an isometric view of a barrel indexing feature and a port body indexing feature.

FIG. 16 shows an isometric view of the barrel indexing feature 434 and a port body indexing feature 429F that facilitate rotational alignment of the barrel port with either the fill port, catheter port, or drainage port on the port body 420. In the position shown in FIG. 16, the barrel port shown at 436 in FIG. 11, (which is aligned with the barrel indexing feature as shown in FIG. 11) is aligned with the fill port, 424 in FIG. 16, and with the fill port indexing feature 429F. The catheter port indexing feature is partially visible at 429C and is located at a 90-degree rotation of the port body 420 relative to the barrel 430. If the barrel 430 were to be rotated 90 degrees to align the barrel indexing feature 434 with the catheter port indexing feature 429C, the barrel port (436 in FIG. 11) would be aligned with the catheter port 422. If the barrel 430 were rotated another 90 degrees in this same direction, the barrel aperture (436 in FIG. 11) would be aligned with the drainage port 426.

Also shown in FIG. 16 and FIG. 11 is port body rotational position indicator 469. In the embodiment shown the port body rotational position indicator 469 is an arrow located on the cylindrical wall of the cup-shaped port body 420, 90 degrees from the position of the fill port and opposite of the catheter port 422. This location for the port body rotational position indicator 469 was chosen so this indicator is on top of the port body 420 when the central axis of the syringe is horizontal and the syringe catheter port is down, the most natural ergonomic position for operating the multi-port syringe. The arrow on the port body rotational position indicator 469 points to a barrel rotational position indicator, shown at 439F in FIG. 16 and at 439D in FIG. 11. In the view of the embodiment shown in FIG. 16, the barrel rotational position indicator 439F is the word "Fill" that located on the cylindrical body of the barrel 430. In the view of the embodiment shown in FIG. 11, the barrel rotational position indicator is the word "Drain" that is located on the cylindrical body of the barrel 430.

5. Port Configurations on the Syringe

Figure 17:
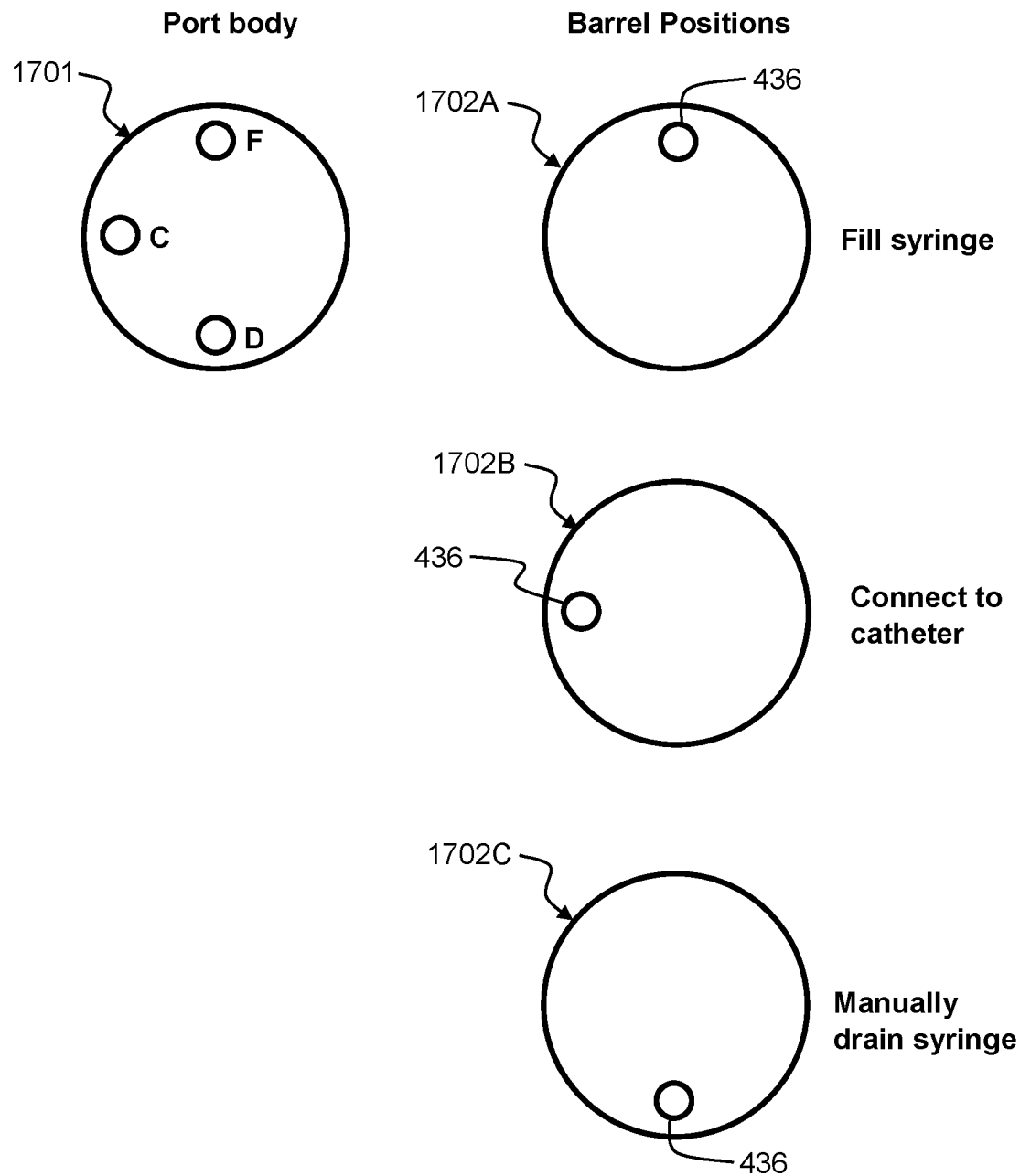
FIG. 17 shows how the rotation of the barrel inside the port body of the 3-port 3-position syringe comprising three axial ports of FIG. 10A through FIG. 16 allows the contents of the barrel to be selectively connected to the fill, catheter, and drain ports of the port body.

FIG. 17 shows a schematic of how the rotation of the barrel inside the port body of a 3-position syringe can be used to allow the content of the barrel to be selectively connected to the fill (i.e. input or fill port or "F"), catheter (or "C"), and drainage (or "D") ports. The position of the port body is shown at 1701 and is assumed to be the same for all rotations of the barrel in the second column. The input or fill port "F" in FIG. 17 is a schematic representation of the location of the input or fill port shown at 424 in FIG. 10A to FIG. 16. The catheter port "C" in FIG. 17 is a schematic representation of the location of the catheter port shown at 422 in FIG. 10A to FIG. 16. The drainage port "D" in FIG. 17 is a schematic representation of the location of the drainage port shown at 426 in FIG. 10A to FIG. 16. Three rotational orientations of the barrel are shown at 1702A, 1702B, and 1702C in FIG. 17. In actual usage, the barrel would be located behind and aligned with the port body as was illustrated in FIGS. 10A to 16. For clarity, the selectable positions of the barrel are shown in a column to the right of the port body so that the three selectable rotational positions can be understood more clearly. The barrel port shown at 436 in FIG. 17 is the same axial aperture in the end of the barrel that was shown in FIG. 11, FIG. 12, FIG. 15A, and FIG. 15B. From the schematic illustration in FIG. 17, one can see that:

(a) Having the opening in the barrel 1702A at the 12 o'clock position will allow fluid to flow between the barrel and the "F" (Fill) port. Thus, 1702A shows the barrel at a "Fill syringe" position.

(b) Having the opening of the barrel 1702B at the 9 o'clock position will allow fluid to flow between the barrel and the "C" (Catheter) port. Thus, 1702B shows the barrel at a "Connect to catheter" position.

(c) Having the opening of the barrel 1702C at the 6 o'clock position will allow fluid to flow between the barrel and the "D" (Drainage) port. Thus, 1702C shows the barrel at a "Manually drain syringe" position.

Although the embodiments illustrated in FIGS. 10A to 16 show only a single axial barrel port 436 that interfaces with the port body 420 to allow flow of a fluid an axial direction (i.e. the fluid flows parallel to the central axis of the cylindrical barrel), it should be understood that some or all of the ports in the port body 420 could also interface with the syringe barrel in a radial configuration (i.e. flowing in a direction inwards or outwards from the central axis of the cylindrical barrel). There can also be differences in the amount of rotation of the syringe barrel relative to the port body that is needed to move from one selectable position (or phase) to another selectable position (or phase). The embodiments illustrated in FIGS. 10A to 16 show a 90-degree (¼ circle) rotation for moving from one selectable port position to another. These rotations could be more or less than this and do not need to be an even fraction of a 360-degree circle.

Figure 18:
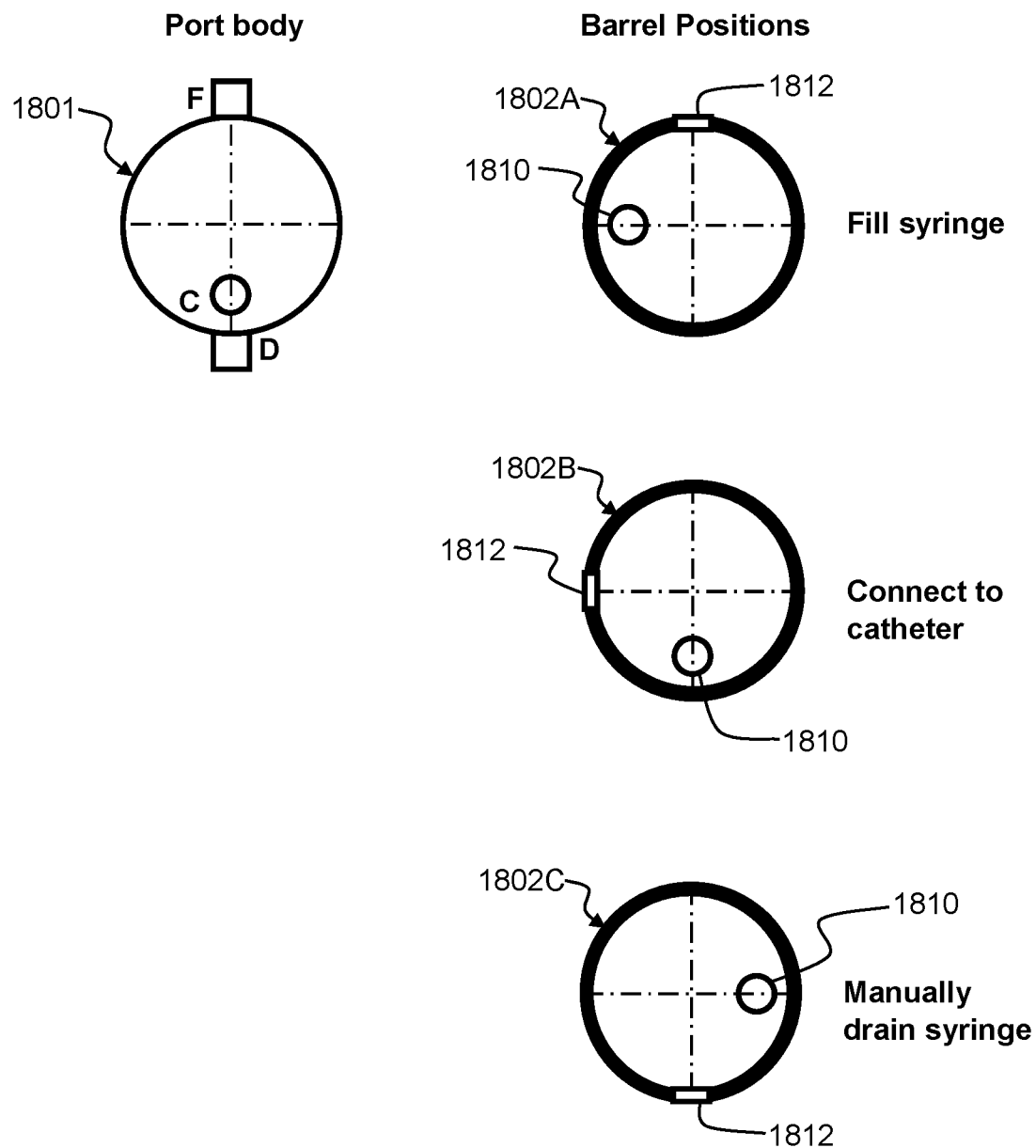
FIG. 18 shows an alternate port body and barrel configuration for a 3-port 3-position syringe in which some ports are axial and some ports are radial.

FIG. 18 shows a schematic of an alternate embodiment of a port body 1801 and three positions of a barrel 1802A, 1802B, and 1802C for a 3-port 3-position syringe. The port body 1801 has one axial port that connects to the catheter and is labeled "C" and two radial ports: fill (i.e. input or fill port or "F"); and drainage (or "D"). The barrel has one axial aperture, shown at 1810 and one radial aperture, shown at 1812. The position of the port body 1801 is assumed to be the same for all rotations of the barrel, 1802A, 1802B, and 1802C in the second column. In actual usage, the barrel (1802A, 1802B, or 1802C) would be located behind and aligned with the port body. For clarity, the selectable positions of the barrel are shown in a column to the right of the port body so that the three selectable rotational positions can be understood more clearly. From this schematic illustration, one can see that:

(a) having the opening in the barrel 1802A at the 12 o'clock position will allow fluid to flow between the barrel and the "F" (Fill) port in a "Fill syringe" position;

(b) having the opening of the barrel 1802B at the 9 o'clock position will allow fluid to flow between the barrel and the "C" (Catheter) port in a "Connect to catheter" position; and (c) having the opening of the barrel 1802C at the 6 o'clock position will allow fluid to flow between the barrel and the "D" (Drainage) port in a "Manually drain syringe" position.

Figure 19:
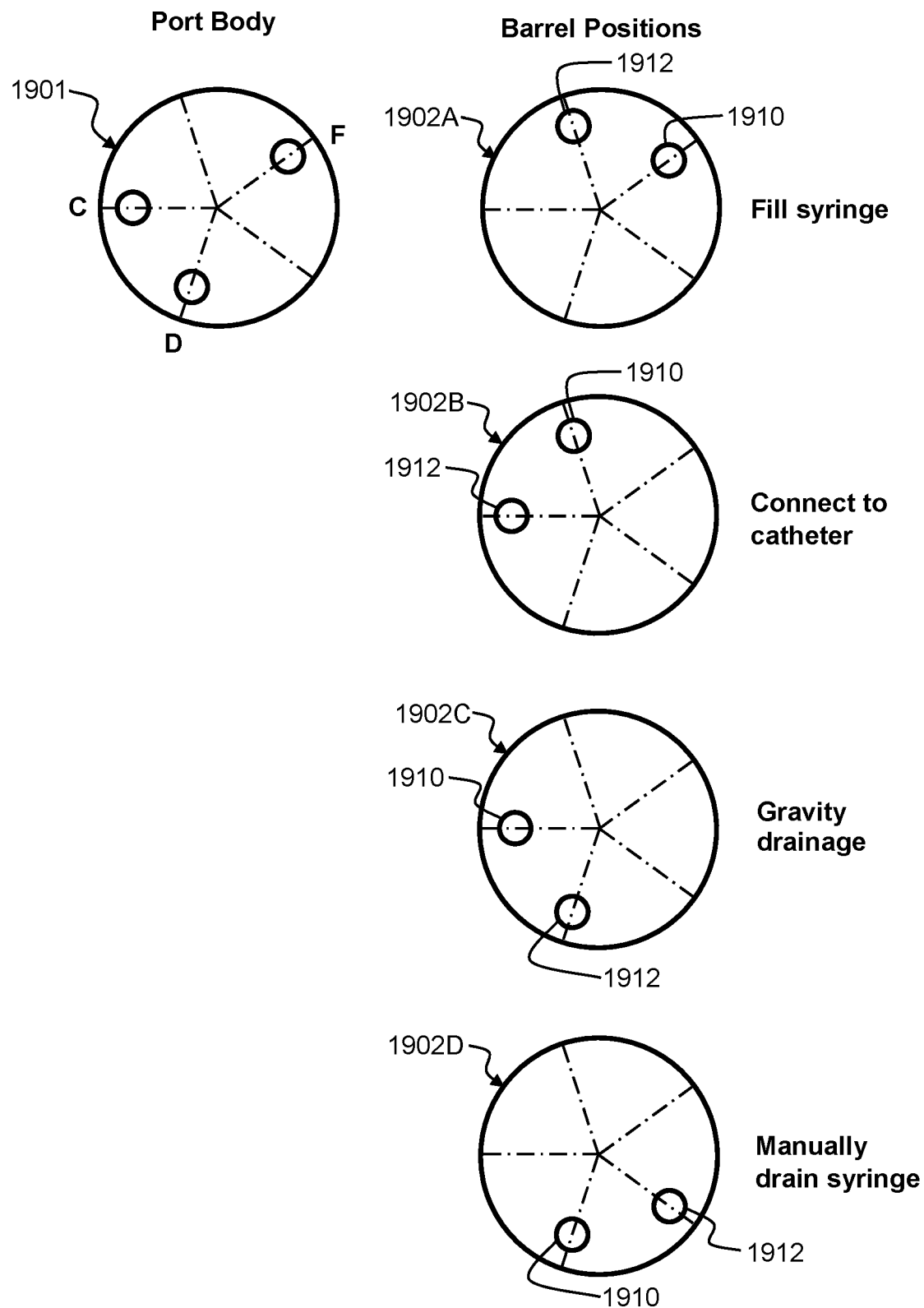
FIG. 19 shows another alternate port body and barrel configuration with all axial ports that can be used to provide selective connection to the fill, catheter, and drain ports and also provide a fourth position for continuous bladder irrigation by connecting the catheter port to the drain port to implement the system shown in FIG. 7 and FIG. 9.

FIG. 19 shows a schematic of another alternate configuration of a port body and barrel that has three ports (Fill or "F", Catheter or "C", and Drainage or "D") in the port body, shown at 1901. As was the case for the schematics shown in FIG. 17 and FIG. 18, the position of the port body 1901 is assumed to be the same for all rotations of the barrel in the second column. The barrel has a first axial aperture, shown at 1910 and a second axial aperture shown at 1912. Four rotational positions of the barrel are shown at 1902A, 1902B, 1902C, and 1902D. In actual usage, the barrel would be located behind and aligned with the port body as was illustrated in FIGS. 10A to 16B. For clarity, the selectable rotations of the barrel are shown in a column to the right of the port body so that the four possible selectable rotations can be understood more clearly. From this schematic illustration, one can see that only four of the five possible equally spaced (72-degree or ⅕$^{th}$ of a 360-degree circle) rotations of the barrel are needed to provide the functions needed for a 4-phase (i.e. 4-position) syringe of the type illustrated at 710 and described with reference to FIG. 7, FIG. 8, and FIG. 9.

Further referring to FIG. 19, the sequence of the four needed selectable rotations, when the barrel is rotated counterclockwise, is:

Barrel in "Fill syringe" orientation 1902A with the first barrel axial aperture 1910 aligned with the "F" (input or fill port) of the port body;

Barrel in "Connect to catheter" orientation 1902B with the second barrel axial aperture 1912 aligned with the "C" (catheter) port of the port body;

Barrel in "Gravity drainage" orientation 1902C, when the Catheter ("C") port is aligned to the first barrel axial aperture 1910 and the Drainage ("D") port is aligned with the second barrel axial aperture 1912; and Barrel in "Manually drain syringe" orientation 1902D when the Drainage ("D") port is aligned with the first barrel axial aperture 1910.

The rotation sequence illustrated in FIG. 19 may not be as ideal as a sequence in the following order: "Fill syringe"; "Connect to catheter"; "Manual drainage"; and "Gravity drainage" because an operator would be using "Fill", "Connect", and "Manual Drainage" while doing manual irrigation and would not want to pass through an unused position as part of the process of going between these three positions. However, the configuration illustrated in FIG. 19 can be implemented using axial ports only. The construction of a syringe system with the functionality illustrated in FIG. 19, FIG. 7, FIG. 8 and FIG. 9 would therefore be similar to the 3-phase (3-port/3-position) system illustrated in detail in FIGS. 10A through 17. The primary differences would be:

(a) A different angular spacing of the Fill ("F"), Catheter ("C"), and drainage ("D") ports on the port body;

(b) Two axial apertures in the closed end of the barrel for the system of FIG. 19 instead of the one axial aperture in the closed end of the barrel for the system of FIG. 17;

(c) Rotations of 72 degrees instead of 90 degrees to go from one position to another; and (d) A total of 4 positions instead of 3.

Figure 20:
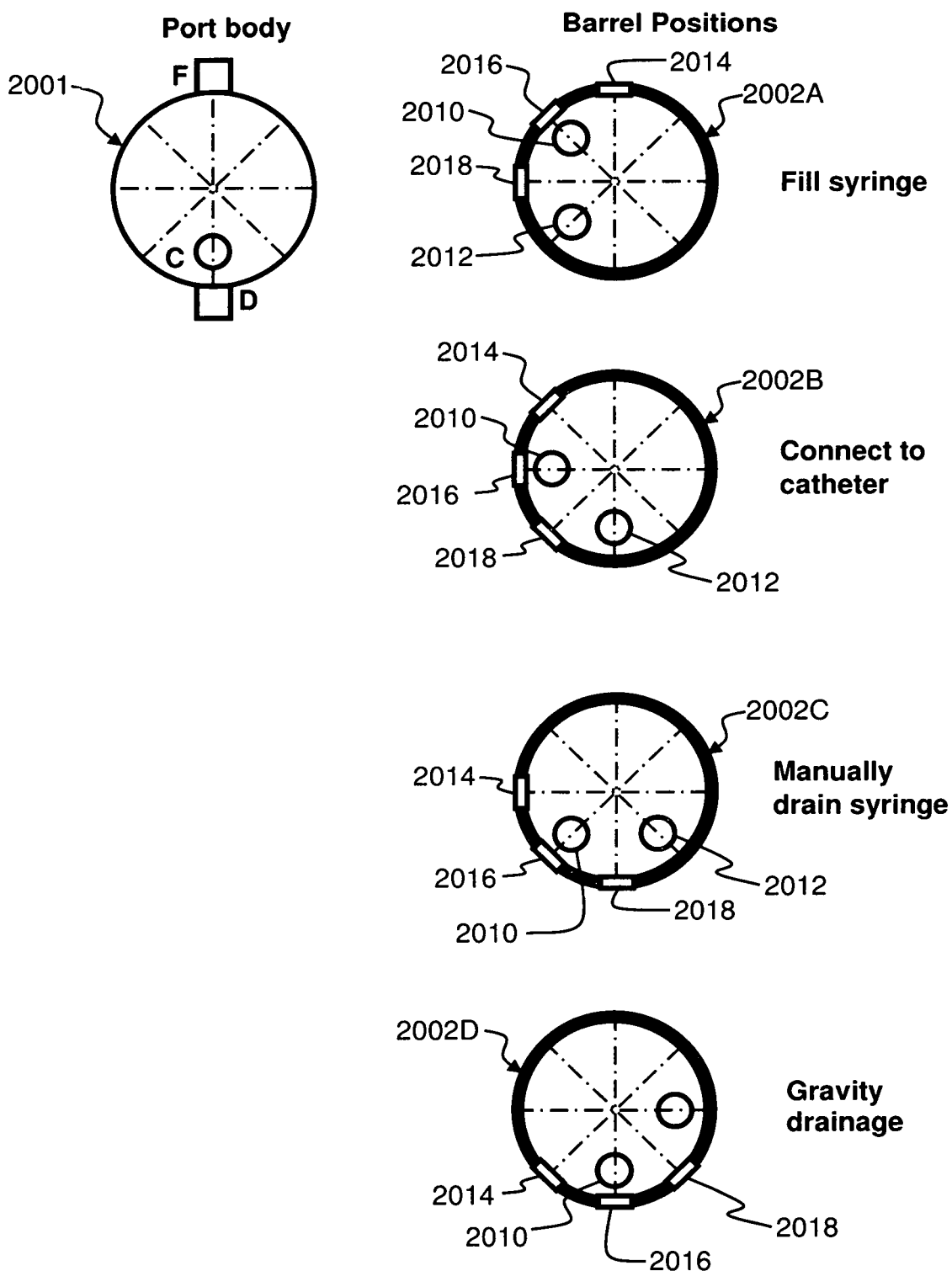
FIG. 20 shows yet another alternate port body and barrel configuration in which two radial ports and one axial port are used to provide selective connection to the fill, catheter, and drain ports, and also provide a fourth position for continuous bladder irrigation by connecting the catheter port to the drain port to implement the system shown in FIG. 7.

FIG. 20 shows a schematic of yet another alternate configuration of a port body and barrel that has three ports (Fill or "F", Catheter or "C", and Drainage or "D") in the port body, shown at 2001. In the schematic shown in FIG. 20, the fill (or "F") port and the drainage (or "D") port are radial ports and the catheter (or "C") port is an axial port. As was the case for the schematics shown in FIG. 17, FIG. 18, and FIG. 19 the position of the port body 2001 is assumed to be the same for all rotations of the barrel in the second column. The barrel has a first barrel axial aperture, shown at 2010, a second barrel axial aperture shown at 2012, a first barrel radial aperture shown at 2014, a second barrel radial aperture shown at 2016, and a third barrel radial aperture shown at 2018. Four rotational positions of the barrel are shown at 2002A, 2002B, 2002C, and 2002D. In actual usage, the barrel would be located behind and aligned with the port body as was illustrated in FIGS. 10A to 16B. For clarity, the selectable rotations of the barrel are shown in a column to the right of the port body so that the four possible selectable rotations can be understood more clearly. From this schematic illustration, one can see that only four of the eight possible equally spaced (45-degree or ⅛th of a 360-degree circle) rotations of the barrel are needed to provide the functions needed for a 4-phase (i.e. 4-position) syringe of the type illustrated at 710 and described with reference to FIG. 7, FIG. 8, and FIG. 9. These barrel positions and the counter-clockwise sequence they occur in are:

(a) Barrel in "Fill syringe" orientation 2002A;

(b) Barrel in "Connect to catheter" orientation 2002B;

(c) Barrel in "Manually drain syringe" orientation 2002C; and (d) Barrel in "Gravity drainage" orientation 2002D, when the Catheter ("C") port and the Drainage ("D") port in the port body 2001 are both connected to the interior of the barrel.

6. Additional Features and Fields of Use

The ports of the multiport syringe can use any combination of any of the standard connections typically used for such medical applications, including but not limited to catheter tips, large and small luer locks, and various types of tubing. This tubing can also have external fasteners to prevent accidently dislodging of any part of the system from any other part or the system or from the catheter.

The multiport syringe could be made in various volumetric sizes. The barrel of the multiport syringe can have information to indicate syringe volumes as is illustrated by the numbers and lines along the length of the cylinder of the barrel 430 in FIG. 4.

The multiport syringe can be made of a medical grade plastic or a re-usable and sterilizable glass or polymer.

The barrel, piston shaft, and inner lining of the multiport syringe, and/or any other component of the system can have an antimicrobial and/or bacteriostatic coating and/or any other treatment to reduce the spread of pathogens. This may help reduce the risk of infection to and from the patent and the user. In addition, a hydrostatic coating can be used on the inner lining of the syringe to facilitate maximum drainage of the fluid.

As previously noted the catheter tip 422 of the port body would be inserted into the irrigation port 122 of the urinary catheter to initiate manual bladder irrigation. In this connection, the catheter tip typically fits and slips snugly inside the irrigation port and is typically a water tight connection. However, for various reasons including operator movement, high pressure irrigation or patient movement this connection can come apart and therefore contaminate the operator, the patient, the surrounding equipment and area. To help maintain this connection between the catheter tip and the irrigation port of the urinary catheter a fastener could be used to on the outside of this connection. This fastener could consist of three square walls fashioned together in an upside down "U" configuration extending longitudinally for a few centimeters. This fastener would resemble a square shaped cylinder without the bottom fourth wall. The fastener would also have a grip located on its top surface to allow its placement and removal from the connection. The grip would extend upwards a few centimeters with a convex direction facing the urinary catheter. This grip would extend from all three walls of upside down "U" configuration in a continuous fashion forming a concave circular shape. This grip would act as a single or second shield to prevent any splash from an accidental disconnection between the catheter tip and irrigation port of the urinary catheter. Using the grip, the fastener would be placed directly on the outside of the urinary catheter at the level of the irrigation port overlapping the established connection between the catheter tip and the irrigation port. This fastener would crimp down on the established connection to bolster this connection and further minimize risk of accidental dislodging of the multiport syringe 410 and 710 from the urinary catheter 100. Once manual irrigation is no longer needed and the multiport syringe is to be removed, the fastener would then be removed from the established connection using the upward facing grip and the catheter tip would then be extracted from the irrigation port of the urinary catheter. This fastener could be tethered to the port body with a short lanyard or as a separate piece.

The catheter tip of the port body could have a detachable tip adapter to be used with a cystoscope for irrigating through the cystoscope. Typically, a rigid cystoscope is used for examining the bladder 90 through same track the urinary catheter 100 travels through as depicted in FIG. 1, which can also be used in a woman. The cystoscope has three ports which include input and drain ports positioned at 90 degrees from the axial direction of the scope shaft along with a center lumen port which is located at the end of the scope in the axial direction and directly contiguous with the shaft of the scope. The center lumen port which is the largest port on the scope, is used for scope lens and instrument insertion. A bridging instrument, which typically has two ports is used to attach the lens and any instruments, to the central lumen port of the scope. The lens is clamped to the bridging instrument which then attaches the lens to the scope. The bridging instrument also provides a passage and guide for instruments to be passed through the shaft of the scope alongside the lens through its second port. During transurethral procedures, the user attaches a light source and camera to the lens and has irrigation running through the input port and empties the bladder through the drain port. When manual irrigation is needed during cystoscopy, the bridging piece along with the attached lens and any inserted instruments are detached from the scope at the center lumen port and a syringe is then attached with an adapter to allow for manual bladder irrigations to remove blood products, tissue material or any surgical debris. As described in FIG. 5, manual bladder irrigations can then be completed using the syringe as shown in FIG. 4 along with the cystoscope adapter in a similar fashion using the rigid scope in place of a urinary catheter 100. Once manual irrigation is complete the bridging piece can be reattached to the center lumen port along with the lens and instruments. Manual irrigation can then be repeated as needed through the procedure.

The syringe detailed in FIG. 11 could further include an additional port along the shaft of the barrel 430. This additional port could be an outlet that could be located externally on barrel wall between the external grasping features of the barrel 432 and the external indexing feature 434. This additional port (outlet) could be positioned 90 degrees to the axial length of the barrel and could have a stop cock to regulate transmission of fluid to and from the interior of the barrel to an external vessel. The external tip of the outlet could be adaptable for connection with a luer lock or any tubing source. This outlet could be used in either 3-port 3-position syringe FIG. 4 or in a 3-port 4-position syringe FIG. 9. This outlet could be functional once the seal of the plunger was extended passed the aperture of the outlet in barrel's shaft towards the open end of the barrel. This outlet could be used to obtain fluid samples from the interior of the barrel in addition to providing a second port for introducing fluid into the interior of the barrel. With the plunger locked in a partly extended position past the aperture of this outlet and towards the open end of the barrel, this outlet with the stop cock left in an open position can act as a continuous drainage port as well when combined with the alignment of barrel port (or aperture) 436 with the catheter port 422 of the port body 420. This outlet feature would provide a fourth phase or second fourth phase option of continuous gravity drainage for a 3-port 3-position syringe or 3-port 4-position syringe respectively.

In an alternate embodiment of the present invention, the port body that was shown in FIG. 13A, FIG. 13B, FIG. 14A, and FIG. 14B can be a detachable port body with universal application. The detachable port body could be similar to the port body as previously described with the following differences:

(a) The detachable port body could be usable with any syringe that has a luer lock, or any tip adapter at its tip;
(b) The detachable port body could be completely enclosed with a rotating combined gasket conduit combination; and
(c) The detachable port body luer lock or catheter tip could extend outwards at the enclosed end for syringes to attach.

The detachable port body could consist of a cylindrical cup comprising a circular bottom, a rim, and a cylindrical wall separating the circular bottom and the rim but this detachable port body could also be enclosed at the rim level. The top enclosure at the rim level could have a central aperture. As previously noted and illustrated in FIG. 14A the detachable port body could have three circular axial apertures in the port body circular bottom: one for the input or fill port 424, one for the catheter port 422, and one for the drainage port 426. The detachable port body could contain a rotating gasket with a center conduit that would fill the enclosure space. This conduit could then travel between central aperture of the rim enclosure to communicate with the axial apertures at the bottom of the port body through the gasket. The gasket could be of medical grade material that could encase a conduit that could rotate with the conduit as one solid piece. The conduit could extend from the central aperture in the rim enclosure towards the bottom of the port body with an angle in its direction for alignments with the axial ports at the bottom of the port body. Therefore, based on rotation of the combined gasket-conduit combination, the tip of the conduit at the bottom of the port body could be in direct communication with the apertures for the fill, catheter, and drainage ports for exclusive fluid transmission between the conduit and one of the ports (422, 424, or 426). At the rim enclosure level, the conduit could extend outwards through the central aperture of the rim enclosure. This top tip of the conduit could have tip adaptable for attachment of a syringe such as a luer lock adapter, allowing any syringe to be attached to this detachable port body. The upward extending portion of the conduit that could extending from the rim enclosure and could also have a marker extending from the conduit shaft that could rotate with the conduit. This marker could be between the rim enclosure and the syringe attachment portion. The conduit marker could then rotate and align with extending markers on the outer portion of the rim enclosure to allow for locking of the conduit marker at each phase. Thus, when the conduit marker and rim enclosure extending features are aligned, the phase of the syringe could be noted and Fill, Drain and Catheter which could also match the position conduit tip at the bottom of the port body which could be in direct communication with the apertures for the fill, catheter, and drainage ports for exclusive fluid transmission between the conduit and one of the ports (422, 424, or 426) respectively. At this time manual irrigation can employed as discussed in FIG. 5 in a similar fashion with rotation of the syringe attached to the gasket-conduit combination.

One or more of the functions of the system could be implemented using an external valve or valves or an external clamp or clamps. One or more of the functions of the system could be implemented using a valve stopcock valve instead of being actuated through rotation of the barrel relative to the port body. The system could also be implemented by having a 3-port 3-position (i.e. 3-phase) syringe and implementing the fourth phase (continuous irrigation plus continuous drainage) as a bypass to the syringe through the use of one or more clamps or a valves, by for example using one or more 3-position stopcock valves and/or one or more 2-position stopcock valves and opening or closing the appropriate stopcock valves for each of the operations involved in the performance of manual irrigation and/or continuous gravity irrigation. In the 2-stopcock configuration, the input and drain would be on the same stopcock that had a 3-way valve that could rotate between fill, off, and drain.

Embodiments of the present invention are not limited to use in urinary applications. They can be used in any human or veterinary medical application, further examples of which include:

a. Gastric applications, such as with enteral feeding tubes.
b. Automated applications in which the valves and pumping of fluids in the syringe are managed by an automated and/or computerized system.

A number of variations and modifications of the disclosed embodiments can also be used. While the principles of the disclosure have been described above in connection with specific apparatuses and methods, it is to be clearly understood that this description is made only by way of example and not as limitation on the scope of the disclosure.

What is claimed is:

1. A medical multi-port syringe system wherein:
the system comprises a port body, a barrel, and a plunger;
the port body comprises:
  a cylindrical cup comprising a circular bottom, a rim, and a cylindrical wall separating the circular bottom and the rim;
  a first port, wherein the first port comprises an input port configured for connection to a fluid source;
  a second port;
  a third port, wherein the third port comprises a drainage port configured for fluid connection to a drainage fluid storage vessel; and
  at least one port body rotational indexing feature;
the barrel comprises a hollow cylinder with an open end and a circular closed end wherein:
  the circular closed end of the barrel is configured to fit inside the cylindrical cup of the port body;
  the barrel comprises at least one barrel rotational indexing feature configured for engagement with the port body rotational indexing feature;
  a combination of the at least one port body rotational indexing feature and the at least one barrel rotational indexing feature are configured to provide a minimum of three indexing positions at three rotations of the barrel relative to the port body comprising:
    an input port position configured for transmission of fluid from the input port to an interior of the barrel:
    a second port position configured for transmission of fluid between the interior of the barrel and the second port; and
    a drainage port position configured for transmission of fluid from the interior of the barrel to the drainage port;
the barrel comprises a barrel axial alignment feature wherein the barrel axial alignment feature comprises a circular ring around the barrel close to the rim of the cylindrical cup of the port body;
the plunger fits inside the hollow cylinder of the barrel;
the plunger further comprises a circular seal at a sealed end of the plunger wherein the seal is configured for restricting the flow of fluid between the sealed end of the plunger and the interior of the hollow cylinder of the barrel;

the plunger is configured to travel axially inside the hollow cylinder of the barrel to increase and decrease the quantity of a fluid in a cylindrical barrel volume defined by the hollow cylinder, the circular closed end of the barrel, and the sealed end of the plunger; and the plunger comprises a grasping feature wherein:
the grasping feature of the plunger is located on the opposite end of the plunger from the seal of the plunger; and
the grasping feature of the plunger is configured for manual axial movement of the plunger relative to the barrel.

2. The medical multi-port syringe system as recited in claim 1, wherein:
the system is a closed urinary syringe system configured for manually irrigating a bladder;
the second port comprises a catheter port configured for fluid connection to a first lumen on a first end of a catheter;
the catheter further comprises a second lumen comprising a balloon configured for retention of a second end of the catheter in the bladder;
the circular closed end of the barrel further comprises:
a raised cylindrical boss located in a center of the circular closed end of the barrel; and
a barrel closed end aperture that is configured for axial flow of a fluid between the interior of the barrel and a port selected from a group of the input port, the catheter port, and the drainage port;
the system further comprises a gasket wherein:
the gasket is circular;
the gasket comprises a central circular aperture that fits around the raised cylindrical boss of the barrel;
the gasket comprises at least one aperture configured for transmission of fluid between an interior of the barrel and a port selected from the group of the input port, the catheter port, and the drainage port; and
the gasket is retained between the circular closed end of the barrel and the circular bottom of the port body by a fastening member that also retains the closed end of the barrel inside the circular bottom of the port body;
the system further comprises the barrel axial alignment feature wherein:
the barrel axial alignment feature is configured for aligning a central axis of the hollow cylinder of the barrel with the central axis of the cylindrical cup of the port body;
the barrel axial alignment feature comprises a circular ring located on the hollow cylinder of the barrel; and
the barrel axial alignment feature is located near to the rim of the port body when the system is assembled;
the system further comprises a first O-ring seal wherein:
the first O-ring seal is configured for preventing a leakage of fluid between the cylindrical cup of the port body and the barrel;
the first O-ring seal is located on an interior of the cylindrical wall and on the exterior of the barrel; and
the first O-ring seal is located between the barrel alignment feature and the circular bottom of the cylindrical cup of the port body;
the system further comprises an input check valve located in the fluid path between the fluid source and the cylindrical barrel volume wherein the input check valve is configured for preventing the flow of fluid from the cylindrical barrel volume toward the fluid source;
the system further comprises a drainage fluid check valve located in a fluid path between the cylindrical barrel volume and the drainage fluid storage vessel wherein the drainage fluid check valve is configured for preventing the flow of fluid from the drainage fluid storage vessel toward the cylindrical barrel volume;
the port body rotational indexing feature is located on the rim of the cylindrical cup; and
the barrel rotational indexing feature is located on the exterior of the barrel.

3. The medical multi-port syringe system as recited in claim 2, wherein:
the system further comprises the catheter;
the gasket further comprises a medical grade elastomeric material;
the gasket further comprises at least three apertures configured for transmission of fluid to and from the interior of the barrel wherein:
centers of the at least three fluid apertures in the gasket are equidistant from the central circular aperture of the gasket;
a distance from a center of the raised cylindrical boss on the barrel to a center of the barrel closed end aperture is the same as a distance from the central circular aperture to the centers of the three fluid apertures in the gasket;
a first fluid aperture in the gasket is configured for exclusive transmission of fluid from the input port to the cylindrical barrel volume when the system is in the input port position;
a second fluid aperture in the gasket is configured for exclusive transmission of fluid between the catheter port and the cylindrical barrel volume when the system is in the catheter port position; and
a third fluid aperture in the gasket is configured for exclusive transmission of fluid from the interior of the barrel to the drainage port when the system is in the drainage port position;
the barrel rotational indexing feature comprises a raised area on the exterior of the barrel;
the port body rotational indexing feature comprises a minimum of three axial protrusions on the rim of the cylindrical cup;
the system further comprises a second O-ring seal wherein the second O-ring seal is configured to sit in a space between a barrel attachment boss, the port body and the fastening member;
the barrel further comprises an attachment feature configured for holding a strap;
an exterior of the port body further comprises a port body rotational position indicator comprising an arrow;
the exterior of the barrel further comprises at least one barrel rotational position indicator;
the barrel further comprises syringe barrel volume information wherein the syringe barrel volume information comprises numbers and lines along a length of an outside of the barrel;
the system further comprises a plunger cover wherein:
the plunger cover wraps around a plunger shaft; and
the plunger cover is located near the open end of the barrel;
the system further comprises a splash shield located near the catheter port wherein the splash shield is configured for reducing an exposure of medical personnel to a content of the catheter if the port body should accidentally become disengaged from the catheter; and
the system further comprises a treatment that reduces a spread of pathogens.

4. The medical multi-port syringe system as recited in claim 1, wherein:
the combination of at least one port body rotational indexing feature and the at least one barrel rotational indexing feature are configured to provide four indexing positions at four rotations of the port body relative to the barrel comprising:
the input port position;
the second port position;
drainage port position; and
a continuous gravity drainage position configured for continuous gravity transmission of fluid between the second port and the drainage port wherein the continuous gravity drainage position does not require manual pumping of the plunger for the continuous gravity transmission of fluid between the second port and the drainage port; and
the system further comprises a plunger axial movement restriction element wherein the plunger movement restriction element is configured for limiting axial motion of the plunger inside the barrel.

5. The medical multi-port syringe system as recited in claim 1, wherein:
the system is configured for transmission of fluid in an axial direction that is parallel to the central axis of the cylindrical barrel:
between the input port and the cylindrical barrel volume;
between the cylindrical barrel volume and the second port; and
between the cylindrical barrel volume and the drainage port.

6. The medical multi-port syringe system as recited in claim 1, wherein:
the system is configured for transmission of fluid in a radial direction between the cylindrical barrel volume and at least one port selected from the group of the input port, the second port, and the drainage port; wherein radial direction comprises a direction flowing perpendicular to the central axis of the cylindrical barrel.

7. The medical multi-port syringe system as recited in claim 1, wherein:
the second port comprises a catheter port configured for a fluid connection to a first lumen on a first end of a catheter;
the system further comprises the catheter;
the system is a closed urinary syringe system configured for irrigating a bladder; and
the catheter further comprises a second lumen comprising a balloon configured for retention of a second end of the catheter in the bladder.

8. The medical multi-port syringe system as recited in claim 1, wherein:
the circular closed end of the barrel further comprises a raised cylindrical boss located in a center of the circular closed end of the barrel; and
the system further comprises a gasket wherein:
the gasket is circular;
the gasket comprises a central circular aperture that fits around the barrel raised cylindrical boss;
the gasket comprises at least one aperture configured for transmission of fluid between the interior of the barrel and a port selected from a group of the input port, the second port, and the drainage port; and
the gasket is retained between the circular closed end of the barrel and the circular bottom of the port body.

9. The medical multi-port syringe system as recited in claim 1, wherein:
the system further comprises the barrel axial alignment feature wherein:
the barrel alignment feature is configured for aligning a central axis of the hollow cylinder with the central axis of the cylindrical cup of the port body;
the barrel alignment feature comprises a circular ring located on the barrel; and
the barrel alignment feature is located near to the rim of the cylindrical cup of the port body when the system is assembled; and
the system further comprises a first O-ring seal wherein:
the first O-ring seal is configured for preventing a leakage of a fluid between the cylindrical cup of the port body and the barrel;
the first O-ring seal is located on an interior of the cylindrical wall and on the exterior of the barrel; and
the first O-ring seal is located between the barrel alignment feature and the circular bottom.

10. The medical multi-port syringe system as recited in claim 1, wherein:
the system further comprises an input check valve located in a fluid path between the fluid source and the cylindrical barrel volume wherein the input check valve is configured for preventing a flow of a fluid from the cylindrical barrel volume toward the fluid source; and
the system further comprises a drainage fluid check valve located in the fluid path between the cylindrical barrel volume and the drainage fluid storage vessel wherein the drainage fluid check valve is configured for preventing a flow of fluid from the drainage vessel toward the barrel.

11. The medical multi-port syringe system as recited in claim 1, wherein:
the system further comprises a gasket wherein:
the gasket is circular; and
the gasket comprises a central circular aperture;
the gasket further comprises at least three apertures configured for transmission of fluid to and from the interior of the barrel wherein:
centers of the at least three fluid apertures in the gasket are equidistant from the central circular aperture of the gasket;
a distance from a center of the raised cylindrical boss on the barrel to a center of the barrel closed end aperture is the same as a distance from the central circular aperture to the centers of the three fluid apertures in the gasket;
a first fluid aperture in the gasket is configured for exclusive transmission of fluid from the input port to the cylindrical barrel volume when the system is in the input port position;
a second fluid aperture in the gasket is configured for exclusive transmission of fluid between the catheter port and the cylindrical barrel volume when the system is in the catheter port position; and
a third fluid aperture in the gasket is configured for exclusive transmission of fluid from the interior of the barrel to the drainage port when the system is in the drainage port position;
the at least one port body rotational indexing feature is located on the cylindrical cup rim; and the at least one barrel rotational indexing feature is located on the exterior of the barrel hollow cylinder;
the barrel rotational indexing feature comprises a raised area on the exterior of the barrel hollow cylinder; and
the at least one port body rotational indexing feature comprises a minimum of three axial protrusions on the rim of the cylindrical cup.

12. The medical multi-port syringe system as recited in claim 1, wherein:
the circular closed end further comprises a raised cylindrical boss located in a center of the circular closed end;
the circular closed end is retained inside the circular bottom of the cylindrical cup of the port body by a fastening member; and
the system further comprises an O-ring seal wherein the O-ring seal is configured to sit in a space between a barrel attachment boss, the port body, and the fastening member.

13. The medical multi-port syringe system as recited in claim 1, wherein:
the barrel further comprises an attachment feature configured for holding a strap;
an exterior of the port body further comprises a port body rotational position indicator comprising an arrow;
an exterior of the barrel further comprises at least one barrel rotational position indicator;
the barrel further comprises syringe barrel volume information wherein the syringe barrel volume information comprises numbers and lines along a length of an outside of the barrel;
the system further comprises a plunger cover wherein the plunger cover wraps around a plunger shaft;
the system further comprises a splash shield located near the catheter port wherein the splash shield is configured for reducing an exposure of medical personnel to a content of the catheter if the port body should accidentally become disengaged from the catheter; and
the system further comprises a treatment that reduces a spread of pathogens.

14. A multi-port syringe system for medical usage wherein:
the system comprises a port body, a barrel, and a plunger;
the port body comprises:
a port body cylindrical cup comprising:
a circular base;
a rim;
a cylindrical wall separating the circular base and the rim;
a first port;
a second port; and
a third port; and
a port body rotational indexing feature;
the barrel comprises:
a barrel hollow cylinder with an open end and a circular closed end wherein the circular closed end of the barrel hollow cylinder is configured to fit inside the port body cylindrical cup;
a barrel axial alignment feature wherein the barrel axial alignment feature comprises a circular ring around the barrel close to the rim of the port body cylindrical cup;
a barrel rotational indexing feature configured to engage with the port body rotational indexing feature and to provide three indexing positions at three rotations of the port body relative to the barrel comprising:
a first rotational indexing position configured for transmission of fluid through the first port to an interior of the barrel;
a second rotational indexing position configured for transmission of fluid through the second port to and from the interior of the barrel; and
a third rotational indexing position configured for transmission of fluid from the interior of the barrel to a storage vessel through the third port;
the plunger fits inside the barrel hollow cylinder; and
the plunger is configured to travel axially inside the barrel hollow cylinder to increase and decrease quantity of a fluid in a cylindrical barrel volume defined by the barrel hollow cylinder, the barrel circular closed end, and the plunger.

15. The multi-port syringe system for medical usage of claim 14, wherein:
the plunger comprises:
a circular elastomeric cap configured for restricting a flow of fluid between a sealed end of the plunger and the interior of the barrel; and
a plunger grasping feature wherein:
the plunger grasping feature is located on the opposite end of the plunger from a plunger seal; and
the plunger grasping feature is configured for manual axial movement of the plunger relative to the barrel.

16. The multi-port syringe system for medical usage of claim 14, wherein:
the first port comprises a first aperture in the circular base of the port body cylindrical cup;
the second port comprises a second aperture in the circular base of the port body cylindrical cup;
the third port comprises a third aperture in the circular base of the port body cylindrical cup; and
the barrel circular closed end comprises a barrel port wherein:
the barrel port is rotationally aligned with the first port when the port body and the barrel are in the first rotational indexing position;
the barrel port is rotationally aligned with the second port when the port body and the barrel are in the second rotational indexing position; and
the barrel port is rotationally aligned with the third port when the port body and the barrel are in the third rotational indexing position.

17. The multi-port syringe system for medical usage of claim 14, wherein:
a circular elastomeric gasket is located between the circular base of the port body circular cup and the circular closed end of the barrel; and
an O-ring seal is located between an exterior of the barrel and an interior of the port body cylindrical cup.

18. The multi-port syringe system for medical usage of claim 14, wherein:
the barrel rotational indexing feature comprises a raised area on an exterior of the barrel hollow cylinder; and
the port body rotational indexing feature comprises three axial protrusions on the rim of the port body cylindrical cup.

19. A syringe system for medical usage comprising a plurality of ports wherein:
the system comprises a port body, a barrel, and a plunger;
the port body comprises a port body cylindrical cup further comprising a circular base, an input port, a catheter port, a drainage port, and at least one port body rotational position feature; and the barrel comprises a hollow cylinder with an open end, a closed end, and a barrel rotational indication feature;

the barrel further comprises a barrel axial alignment feature wherein the barrel axial alignment feature comprises a circular ring around the barrel close to the rim of the cylindrical cup of the port body;

the barrel is located with the closed end inside the port body cylindrical cup;

the input port is configured for connection to a fluid source;

the catheter port is configured for connection to a catheter;

the drainage port is configured for connection to a storage vessel;

the plunger comprises a plunger seal;

the plunger is at least partway inside the barrel;

the system is configured for:
  rotating the port body relative to the barrel to an input port position by aligning a first port body rotational feature with the barrel rotational indication feature;
  manually retracting the plunger at least partway toward the open end of the barrel to transmit fluid from the input port to an interior of the barrel;
  rotating the port body relative to the barrel to a catheter port position by aligning a second port body rotational feature with the barrel rotational indication feature;
  manually inserting the plunger at least partway toward the closed end of the barrel to transmit fluid from the interior of the barrel to the catheter port;
  manually retracting the plunger at least partway toward the open end of the barrel to transmit fluid from the catheter port to the interior of the barrel;
  rotating the port body relative to the barrel to a drainage port position by aligning the third port body rotational feature with the barrel rotational indication feature; and
  manually inserting the plunger at least partway toward the closed end of the barrel to transmit fluid from the interior of the barrel to the drainage port.

20. The syringe system of claim 19 wherein:

the input port comprises a first aperture in the circular base of the cylindrical cup;

the catheter port comprises a second aperture in the circular base of the cylindrical cup;

the drainage port comprises a third aperture in the circular base of the cylindrical cup; and the barrel closed end comprises a barrel port configured for rotational alignment with:
  the first aperture when the port body and the barrel are rotated to the input port position;
  the second aperture when the port body and the barrel are rotated to the catheter port position; and
  the third aperture when the port body and the barrel are rotated to the drainage port position.

* * * * *